(12) United States Patent
Weiss et al.

(10) Patent No.: US 11,759,556 B2
(45) Date of Patent: Sep. 19, 2023

(54) PARABIOTIC DIALYSIS SYSTEMS AND TECHNIQUES

(71) Applicants: Fresenius Medical Care Deutschland GmbH, Bad Homburg (DE); Fresenius Medical Care Holdings, Inc., Waltham, MA (US); Fresenius Medical Care AG & Co. KGaA, Bad Homburg (DE)

(72) Inventors: Stefan Weiss, Bad Homburg (DE); Peter Kotanko, New York, NY (US); Roland Sander, St. Wendel (DE)

(73) Assignees: Fresenius Medical Care Holdings, Inc., Waltham, MA (US); Fresenius Medical Care Deutschland GmbH, Bad Homburg (DE); Fresenius Medical Care AG & Co. KGaA, Bad Homburg (DE)

( * ) Notice: Subject to any disclaimer, the term of this patent is extended or adjusted under 35 U.S.C. 154(b) by 288 days.

(21) Appl. No.: 17/352,656

(22) Filed: Jun. 21, 2021

(65) Prior Publication Data
US 2022/0008633 A1    Jan. 13, 2022

Related U.S. Application Data

(60) Provisional application No. 63/049,296, filed on Jul. 8, 2020.

(51) Int. Cl.
*A61M 1/16*    (2006.01)

(52) U.S. Cl.
CPC ....... *A61M 1/1601* (2014.02); *A61M 2230/00* (2013.01); *A61M 2250/00* (2013.01)

(58) Field of Classification Search
CPC .... A61M 1/1601; A61M 1/3621; A61M 1/16; A61M 1/14; A61M 1/34; A61M 2230/00;
(Continued)

(56) References Cited

U.S. PATENT DOCUMENTS 3,682,172 A * 8/1972 Freedman ............ B01D 65/102
                                                    604/7
3,699,960 A   10/1972 Freedman
(Continued)

FOREIGN PATENT DOCUMENTS

EP    0615780 B1    4/2001
EP    1547628 A4    2/2008
(Continued)

OTHER PUBLICATIONS

CNIPA, Chinese Application No. 201880079770.6, Second Office Action dated Apr. 29, 2022, English and Chinese translations, 14 pages.

(Continued)

*Primary Examiner* — Ariana Zimbouski
(74) *Attorney, Agent, or Firm* — Bass Patent Law, LLC

(57) ABSTRACT

The present teachings generally include parabiotic dialysis systems and techniques. For example, the present disclosure includes parabiotic liver dialysis, e.g., for use in settings with limited resources. To this end, a parabiotic liver dialysis system may include a device having a semipermeable membrane with an average pore size that allows for the passage of albumin therethrough. In such a system, a first extracorporeal circuit may connect the device to the vascular system of a first animal (e.g., a liver patient), and a second extracorporeal circuit may connect the device to the vascular system of a second animal (e.g., a human with normal liver function), where the exchange of albumin therebetween is facilitated through the device. The present disclosure also includes various safety measures for parabiotic dialysis systems and techniques, such as biometric verification systems and techniques.

16 Claims, 10 Drawing Sheets

(58) Field of Classification Search
CPC .. A61M 2250/00; B01D 61/243; B01D 61/32
See application file for complete search history.

(56) References Cited

U.S. PATENT DOCUMENTS

| | | | |
|---|---|---|---|
| 5,151,082 A * | 9/1992 | Gorsuch | A61M 1/1643 210/645 |
| 5,628,959 A | 5/1997 | Kross | |
| 6,114,176 A | 9/2000 | Edgson et al. | |
| 8,932,469 B2 | 1/2015 | Childers et al. | |
| 10,086,123 B2 | 10/2018 | Welzel et al. | |
| 10,391,220 B2 | 8/2019 | Kotanko et al. | |
| 2003/0129736 A1 | 7/2003 | Mitrani | |
| 2004/0024342 A1 | 2/2004 | Weitzel et al. | |
| 2004/0044302 A1* | 3/2004 | Bernard | A61M 1/3621 210/348 |
| 2006/0041995 A1 | 3/2006 | Toth | |
| 2009/0120873 A1* | 5/2009 | Becker | B01D 65/02 210/636 |
| 2012/0103902 A1 | 5/2012 | Childers et al. | |
| 2012/0305486 A1* | 12/2012 | Storr | A61M 1/16 210/500.21 |
| 2013/0199998 A1 | 8/2013 | Kelly et al. | |
| 2013/0317837 A1* | 11/2013 | Ballantyne | A61M 1/3627 705/2 |
| 2014/0284275 A1 | 9/2014 | Boccato et al. | |
| 2017/0173251 A1 | 6/2017 | Doyle et al. | |
| 2017/0173253 A1 | 6/2017 | Funkhouser | |
| 2019/0336670 A1 | 11/2019 | Kotanko et al. | |

FOREIGN PATENT DOCUMENTS

| | | | |
|---|---|---|---|
| EP | 1572330 B1 | 11/2010 | |
| EP | 2380610 A1 | 10/2011 | |
| WO | 2009094185 A2 | 7/2009 | |
| WO | WO-2013028809 A2 * | 2/2013 | ......... A61M 1/16 |
| WO | 2018071869 A1 | 4/2018 | |
| WO | 2019139671 A1 | 7/2019 | |
| WO | 2020062135 A1 | 4/2020 | |
| WO | 2022010635 | 1/2022 | |

OTHER PUBLICATIONS

Sun Shilan, et al. ed., "New Theory and New Technology of Hemopurification," Henan Science and Technology Press, 1st Edition, Sep. 30, 2017, Chinese and English translations, 5 pages.

Wu Kaichun et al. ed., China Medical Science Press, 1st Edition, Jun. 30, 2017, Chinese and English translations, 9 pages.

ISA/EP, "International Search Report and Written Opinion dated Nov. 19, 2021," PCT Application No. PCT/US21/38192, 18 Pages.

"Liver support system," Wikipedia, https://en.wikipedia.org/wiki/Liver_support_system, last edited on Feb. 2, 2020. 39 Pages.

"Plasmapheresis," Wikipedia, https://en.wikipedia.org/wiki/Plasmapheresis, last edited on Mar. 20, 2020. 7 pages.

Boada, et al., "Treatment of Alzheimer disease using combination therapy with plasma exchange and haemapheresis with albumin and intravenous immunoglobulin: Rationale and treatment approach of the AMBAR (Alzheimer Management By Albumin Replacement)," Sociedad Española de Neurología, 31: pp. 473-481 (2016).

Breimer et al. "Extracorporeal ("ex vivo") connection of pig kidneys to humans. I. Clinical data and studies of platelet destruction," Xenotransplantation, ISSN 0908-665X, 1996; 3rd Issue, pp. 328-339.

Breimer, et al. "Extracorporeal ("ex vivo") connection of pig kidneys to humans. I. Clinical data and studies of platelet destruction."; Xenotransplantation; Nov. 1996. 2 pages.

CNIPA, Chinese Application No. 201880079770.6, First Office Action dated Sep. 3, 2021, 14 Pages (Chinese and English Translation).

EPO, Application No. EP18899645.8, Extended European Search Report dated Apr. 7, 2021, 10 Pages.

Fresenius Medical Care, "Prometheus@ therapy system for the support of liver function," Product Catalog (2007). 8 Pages.

Fresenius Medical Care, AlbuFlow Filter Spec Sheet (2014). 12 pages.

Gambro, "MARS® system takes over detoxification when the liver can't" (2013). 4 pages.

Horslen, et al. "Extracorporeal Liver Perfusion Using Human and Pig Livers for Acute Liver Failure." Transplantation (online): Nov. 27, 2000 (Nov. 27, 2000)—vol. 70—Issue—p. 1472-1478, 9 pages.

India Patent Office, IN Application No. 202037009001 Examination Report dated Sep. 9, 2021, 7 pages.

ISA, Written Opinion and International Search Report of PCT/US 18161167, dated Dec. 5, 2018. 6 Pages.

Lee, et al., "Extracorporeal liver assist device to exchange albumin and remove endotoxin in acute liver failure: Results of a pivotal pre-clinical study," Journal of Hepatology, vol. 63, pp. 634-642 (2015).

Menendez-Gonzalez, et al., "Albumin Exchange in Alzheimer's Disease: Might CSF Be an Alternative Route to Plasma?," vol. 10, Article 1036 (Oct. 2019). 7 pages.

Parabiotic Dialysis: Its Usefulness as an Experimental Tool; J.A. Pauze et al.; Journal of Applied Physiology, vol. 30, No. 3, Mar. 1971. pp. 420-423.

Parabiotic Dialysis; M. Pavone-Macaluso et al.; From the Department of Physiology, Emory University, Atlanta, Georgia 30322 (Publication No. 620 of the Division of Basic Health Sciences. Supported by grants from the Georgia Heart Association and from U.S. Public Health Service (No. HE-07920). pp. 285-291.

Safiullah, et al. "Development of a Three-Dimensional Kidney Model for Use in a Virtual Reality Environment." UC Irvine: Clinical Translational Science Day UCI, Jun. 13, 2017 (Jun. 13, 2017). 6 Pages.

WIPO, PCT Application No. PCT/US/2018/061167, Notification Concerning ransmittal of International Preliminary Report on Patentability issued by the International Bureau of WIPO, dated Jul. 23, 2020. 6 Pages "U.S. Appl. No. 16/589,581," Notice of Allowance dated Apr. 20, 2022, 7 pages.

"U.S. Appl. No. 16/589,581, Non-Final Office Action dated Mar. 16, 2022," 19 pages.

U.S. Appl. No. 16/511,062, Non-Final Office Action dated Oct. 1, 2021. 15 pages.

CNIPA, "Chinese Application No. 201880079770.6," Decision on Rejection dated Sep. 23, 2022, Chinese and English Translations, 10 pages.

EPO, "Invitation to Pay Additional Fees dated Sep. 29, 2021," PCT Application No. PCT/US21/38192, 15 pages.

"U.S. Appl. No. 16/511,062 Notice of Allowance dated Dec. 14, 2021," 7 pages.

* cited by examiner

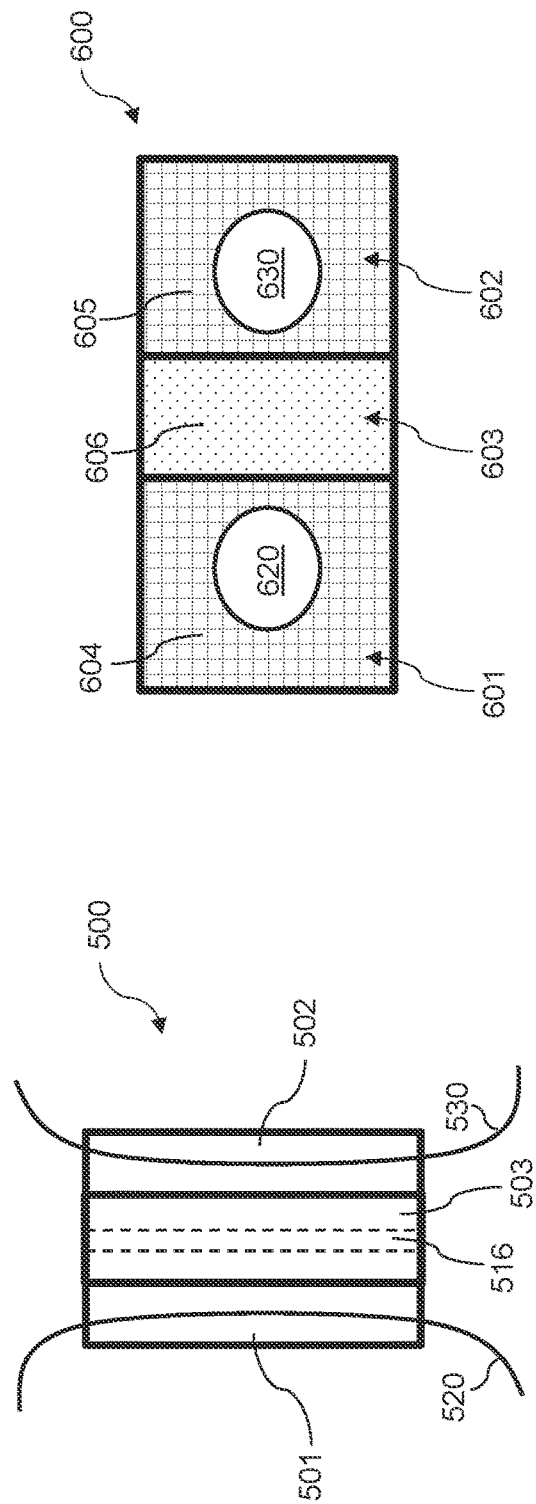
FIG. 5
FIG. 6
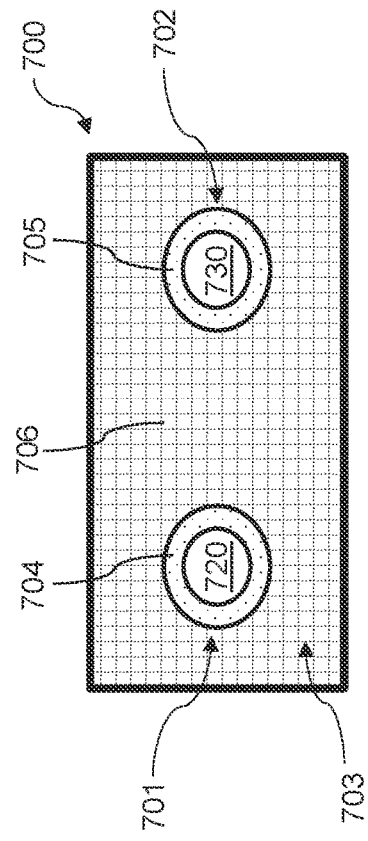
FIG. 7

PARABIOTIC DIALYSIS SYSTEMS AND TECHNIQUES

CROSS-REFERENCE TO RELATED APPLICATIONS

This application claims priority to U.S. Provisional Patent Application No. 63/049,296 filed on Jul. 8, 2020, the entire contents of the foregoing application are hereby incorporated by reference herein.

FIELD

The present disclosure generally relates to parabiotic dialysis systems and techniques. For example, the present disclosure includes devices, systems, and methods for parabiotic liver dialysis as well as various safety measures for parabiotic dialysis systems and techniques.

BACKGROUND

Liver dialysis is a detoxification treatment for patients with liver disorders (e.g., acute liver failure, decompensated chronic liver disease, hepatorenal syndrome, liver failure after liver surgery, secondary liver failure, multi-organ failure, intractable pruritus in cholestasis, and the like), where liver dialysis is similar to, and generally based on the same principles as, hemodialysis. However, unlike hemodialysis, which is used for kidney failure and typically involves the removal of water-soluble toxins from a patient's bloodstream, liver dialysis seeks to remove toxins bound to albumin that accumulate from liver failure. That is, liver dialysis typically involves artificial extracorporeal liver support, where artificial filtration and absorption devices are used to remove lipophilic, albumin-bound substances such as bilirubin, bile acids, metabolites of aromatic amino acids, medium-chain fatty acids, and cytokines from a patient's bloodstream.

Liver dialysis is typically performed by physicians, surgeons, and specialized nurses. Because of the need for these experts, liver dialysis is usually only available in larger hospitals, e.g., hospitals connected with medical schools. Some existing types of liver dialysis will now be discussed by way of example. Single pass albumin dialysis (SPAD) is a relatively simple method of albumin dialysis using standard renal replacement therapy machines without an additional perfusion pump system. In SPAD, a patient's blood flows through a circuit with a high-flux hollow fiber hemodiafilter, where the other side of this membrane is cleansed with an albumin solution in a counter-directional flow, which is discarded after passing the filter. Another type of liver dialysis is the molecular adsorbents recirculation system (MARS®), which involves the use of two separate dialysis circuits—the first circuit includes human serum albumin in contact with a patient's blood through a semipermeable membrane, and the second circuit includes a hemodialysis machine that is used to clean the albumin in the first circuit before it is recirculated to the semipermeable membrane in contact with the patient's blood. Yet another type of liver dialysis uses a Prometheus® device developed by Fresenius Medical Care (where Prometheus® is a registered trademark of Fresenius Medical Care) that combines high-flux hemodialysis with albumin adsorption in a secondary circuit and selective filtration/separation of the albumin fraction through a specific polysulfon filter (e.g., an AlbuFlow® filter, where AlbuFlow® is a registered trademark of Fresenius Medical Care). In each of the aforementioned examples of liver dialysis, a power source (e.g., electricity) and fresh water (e.g., for the dialysate) are usually needed. Thus, liver dialysis treatments may be unavailable in environments where access to such resources is limited, e.g., regions with developing or unreliable infrastructure (e.g., third-world countries or economically-challenged areas), undeveloped regions, and disaster-stricken areas (e.g., a developed region affected by a natural disaster, military conflict, or the like that has temporarily disabled its infrastructure).

There remains a need to provide parabiotic liver dialysis systems and techniques, e.g., for settings with limited resources. There also remains a need to provide parabiotic liver dialysis systems and techniques with improved efficacy. Moreover, there remains a need for safety measures for parabiotic dialysis systems and techniques.

SUMMARY

The present teachings generally include parabiotic dialysis systems and techniques. For example, the present disclosure includes parabiotic liver dialysis, e.g., for use in settings with limited resources. To this end, a parabiotic liver dialysis system may include a device having a semipermeable membrane with an average pore size that allows for the passage of albumin therethrough (e.g., an average pore size that allows for the passage therethrough of molecules having a molecular weight similar to that of albumin). Moreover, depending on the size of the components of blood in which the membrane is structurally configured to prevent passage therethrough, the membrane may still allow for the passage therethrough of components smaller than red blood cells, e.g., components smaller than low-density lipoprotein (LDL) (which may be about 2700 kilodaltons (kDa)), smaller than immunoglobulin type M (IgM) (which may be about 950 kDa), smaller than immunoglobulin type G (IgG) (which may be about 150 kDa), and/or smaller than endotoxins (which may be about 100 kDa). In such a system, a first extracorporeal circuit may connect the device to the vascular system of a first animal (e.g., a liver patient), and a second extracorporeal circuit may connect the device to the vascular system of a second animal (e.g., a human with normal liver function), where the exchange of albumin therebetween is facilitated through the device. The present disclosure also includes various safety measures for parabiotic dialysis systems and techniques, such as biometric verification systems and techniques.

In an aspect, a parabiotic liver dialysis system disclosed herein may include: a device having a first side and a second side, the device including a semipermeable membrane between the first side and the second side, the semipermeable membrane having an average pore size allowing for passage of molecules having a molecular weight of between about 70 kilodaltons (kda) and 140 kda; a first extracorporeal circuit including one or more first fluid connectors for connecting the first side of the device to the vascular system of a first animal; a second extracorporeal circuit including one or more second fluid connectors for connecting the second side of the device to the vascular system of a second animal; a first pump in fluid communication with at least one of the first and second extracorporeal circuits; and a driver mechanically coupled to the first pump, the driver configured to drive the first pump using energy from an energy source.

Implementations may include one or more of the following features. The molecules may include albumin. The system may be configured such that albumin is transferred from the first animal to the second animal. The molecules may include a water-soluble toxin. The water-soluble toxin may include one or more of ammonia, urea, aromatic amino acids, manganese, and a benzodiazepine-like substance. The first animal may have a liver disorder. The liver disorder may be one or more of acute liver failure, decompensated chronic liver disease, hepatorenal syndrome, liver failure after liver surgery, secondary liver failure, multi-organ failure, hepatic encephalopathy, and cholestasis. The first animal may have jaundice. The first animal may be a human infant. The system may further include a physiological sensor coupled to one or more of the first animal and the second animal. The system may further include a controller in communication with the physiological sensor, the controller configured to control operation of the system at least in part based upon a signal from the physiological sensor. The controller may be configured to pause or stop operation of the system upon receipt of a predetermined signal from the physiological sensor. The physiological sensor may include an oncotic pressure monitor. The oncotic pressure monitor may be structurally configured to detect albumin transfer. The physiological sensor may include a blood volume monitor. The blood volume monitor may be structurally configured to measure protein concentration. The blood volume monitor may use ultrasound. The physiological sensor may be structurally configured to detect fluid loss in one or more of the first animal and the second animal. The physiological sensor may be structurally configured to measure bilirubin. The physiological sensor may be an optical sensor. The physiological sensor may be structurally configured to track a transfer of the molecules through the semipermeable membrane. The system may further include a biometric verification system configured to identify one or more of the first animal and the second animal to determine a permission for use of the system. The system may further include a controller in communication with the biometric verification system and one or more other components of the system, the controller configured to prevent or stop operation of the one or more other components of the system upon receipt of a predetermined signal from the biometric verification system. The biometric verification system may be configured to confirm a compatibility between the first animal and the second animal. The biometric verification system may be in communication with a database containing information regarding one or more of the first animal and the second animal. The biometric verification system may include one or more of a biometric identifier, a fingerprint scanner, a retinal scanner, and a voice identifier. The biometric verification system may be structurally configured to concurrently identify the first animal and the second animal. The biometric verification system may be configured to identify one or more of the first animal and the second animal at least once during operation of the system. The system may further include a controller in communication with the first pump, the controller configured to control a flow rate of one or more of the first extracorporeal circuit and the second extracorporeal circuit. The flow rate may be selected to provide a predetermined fluid balance for one or more of the first animal and the second animal. The flow rate may be adjustable based on a signal received from one or more physiological sensors coupled to one or more of the first animal and the second animal. The device may further include a plurality of chambers, where the semipermeable membrane is disposed within one of the plurality of chambers. A first chamber of the plurality of chambers may include at least part of the first extracorporeal circuit, where a second chamber of the plurality of chambers includes at least part of the second extracorporeal circuit, and where a third chamber of the plurality of chambers is disposed at least partially between the first chamber and the second chamber. The third chamber may at least partially surround the first chamber and the second chamber. The third chamber may contain the semipermeable membrane, where each of the first chamber and the second chamber include different semipermeable membranes. One or more of the first chamber and the second chamber may include the semipermeable membrane. The third chamber may include an interface media. The interface media may be a fluid. One or more of the first animal and the second animal may be a human. One or more of the first animal and the second animal may be a non-human. Blood from one or more of the first animal and the second animal may contain molecules that are desirous for transfer into blood of the other one of the first animal and the second animal. The driver may include a mechanical crank, where the energy source is an animal. The mechanical crank may be a hand crank, where the animal is a human. The driver may include a motor and a photovoltaic cell, where the energy source is light. The driver may include a motor, where the energy source is a battery. The system may further include a second pump. The first pump may be in fluid communication with the first extracorporeal circuit and the second pump may be in fluid communication with the second extracorporeal circuit. The second pump may be mechanically coupled to the driver. One or more of the first pump, the second pump, and the driver may be configured to establish a predetermined pressure gradient between the first and second extracorporeal circuits. The predetermined pressure gradient may be provided at least in part by a predetermined gear ratio difference between the first pump and the second pump. The system may further include a selector switch having at least a first setting and a second setting, the first setting establishing a zero-pressure gradient between the first and second extracorporeal circuits, and the second setting establishing a nonzero pressure gradient between the first and second extracorporeal circuits. The predetermined pressure gradient may be selected to implement a predetermined molecule transfer between the first extracorporeal circuit and the second extracorporeal circuit. The system may further include a resistive element in fluid communication with one or more of the first extracorporeal circuit and the second extracorporeal circuit, the resistive element configured to establish a predetermined pressure gradient between the first and second extracorporeal circuits. The semipermeable membrane may include one or more of a hollow-fiber and a plate. At least one of the one or more first fluid connectors and the one or more second fluid connectors may be primed with an anti-coagulant.

In an aspect, a parabiotic liver dialysis system disclosed herein may include: a device having a first side and a second side, the device including a semipermeable membrane between the first side and the second side, the semipermeable membrane having pores with a pore size structurally configured to allow for passage of albumin therethrough but to prevent passage of antibodies therethrough; a first extracorporeal circuit including one or more first fluid connectors for connecting the first side of the device to the vascular system of a first animal; a second extracorporeal circuit including one or more second fluid connectors for connecting the second side of the device to the vascular system of a second animal; a first pump in fluid communication with at least one of the first and second extracorporeal circuits; and a driver mechanically coupled to the first pump, the driver configured to drive the first pump using energy from an energy source.

Implementations may include one or more of the following features. The pore size may be structurally configured to prevent passage of fibrinogen therethrough. The pore size may be structurally configured to prevent passage of immunogenic substances therethrough. The pore size may be structurally configured to prevent passage of pathogens therethrough. The pathogens prevented from passing through the semipermeable membrane may include one or more of a virus and bacteria.

In an aspect, a method for parabiotic liver dialysis disclosed herein may include: moving blood of a first animal through a first extracorporeal circuit including a first fluid connector that connects a first side of a device to the vascular system of the first animal, the device including a semipermeable membrane having an average pore size allowing for passage of one or more molecules having a molecular weight of between about 70 kilodaltons (kda) and 140 kda; and moving the one or more molecules through the device to a second extracorporeal circuit including a second fluid connector that connects a second side of the device to the vascular system of a second animal.

In an aspect, a method for parabiotic liver dialysis disclosed herein may include: connecting a first side of a device to the vascular system of a first animal to form a first extracorporeal circuit, the device including a semipermeable membrane having an average pore size allowing for passage of molecules having a molecular weight of between about 70 kilodaltons (kda) and 140 kda; and connecting a second side of the device to the vascular system of a second animal to form a second extracorporeal circuit.

Implementations may include one or more of the following features. The method may further include moving blood of the first animal through the first extracorporeal circuit, and moving one or more molecules from the blood of the first animal through the semipermeable membrane to the second extracorporeal circuit.

In an aspect, a method for parabiotic liver dialysis disclosed herein may include: moving blood of a first animal through a first extracorporeal circuit including a first fluid connector that connects a first side of a device to the vascular system of the first animal, the device including a semipermeable membrane having pores with a pore size structurally configured to allow for passage of albumin therethrough but to prevent passage of antibodies therethrough; and moving albumin through the device to a second extracorporeal circuit including a second fluid connector that connects a second side of the device to the vascular system of a second animal.

In an aspect, a method for parabiotic liver dialysis disclosed herein may include: connecting a first side of a device to the vascular system of a first animal to form a first extracorporeal circuit, the device including a semipermeable membrane having pores with a pore size structurally configured to allow for passage of albumin therethrough but to prevent passage of antibodies therethrough; and connecting a second side of the device to the vascular system of a second animal to form a second extracorporeal circuit.

Implementations may include one or more of the following features. The method may further include moving blood of the first animal through the first extracorporeal circuit, and moving albumin from the blood of the first animal through the semipermeable membrane to the second extracorporeal circuit.

In an aspect, a system disclosed herein may include: a device having a first side and a second side, the device including a semipermeable membrane between the first side and the second side that is structurally configured for permitting passage of one or more molecules therethrough; a first extracorporeal circuit including one or more first fluid connectors for connecting the first side of the device to the vascular system of a first animal; a second extracorporeal circuit including one or more second fluid connectors for connecting the second side of the device to the vascular system of a second animal; a biometric verification system configured to identify one or more of the first animal and the second animal to determine a permission for use; and a controller in communication with the biometric verification system, the controller configured to control operation of the system based on one or more signals received from the biometric verification system related to the permission for use.

Implementations may include one or more of the following features. The controller may be configured to prevent or stop operation of the system when there is an indication that one or more of the first animal and the second animal lacks the permission.

In an aspect, a method disclosed herein may include: connecting a first side of a device to the vascular system of a first animal to form a first extracorporeal circuit, the device including a semipermeable membrane structurally configured for permitting passage of one or more molecules therethrough; connecting a second side of the device to the vascular system of a second animal to form a second extracorporeal circuit; identifying and determining a permission for use for each of the first animal and the second animal; and, when it is determined that there is permission for use for each of the first animal and the second animal, moving blood of the first animal through the first extracorporeal circuit thereby moving the one or more molecules from the blood of the first animal through the semipermeable membrane to the second extracorporeal circuit.

In an aspect, a parabiotic liver dialysis system disclosed herein may include: a first extracorporeal circuit, including a first outlet and a first inlet connecting the first extracorporeal circuit to the vascular system of a first animal, and a first pump structurally configured to move blood through the first extracorporeal circuit between the first outlet and the first inlet. The system may further include a second extracorporeal circuit, including: a second outlet and a second inlet connecting the second extracorporeal circuit to the vascular system of a second animal, and a second pump structurally configured to move blood through the second extracorporeal circuit between the second outlet and the second inlet. The system may also include a filtering circuit in fluid communication with the first extracorporeal circuit and the second extracorporeal circuit, the filtering circuit including: a first filter including a first semipermeable membrane having first pores, the first filter structurally configured to filter blood from the first animal flowing through the first extracorporeal circuit; and a second filter including a second semipermeable membrane having second pores, the second filter structurally configured to filter blood from the second animal flowing through the second extracorporeal circuit, where at least some pores of one or more of the first pores and the second pores have a pore size structurally configured to allow for passage of albumin therethrough.

Implementations may include one or more of the following features. The system may further include a first bypass connecting the first extracorporeal circuit to the second extracorporeal circuit, where the first extracorporeal circuit is configured such that a first blood portion flowing through the first filter without passing through the first pores flows back into the vascular system of the first animal through the first extracorporeal circuit, and where a second blood portion passing through the first pores flows through the first bypass and into the second extracorporeal circuit for entering the vascular system of the second animal. The system may also include a second bypass connecting the second extracorporeal circuit to the first extracorporeal circuit, where the second extracorporeal circuit is configured such that a third blood portion flowing through the second filter without passing through the second pores flows back into the vascular system of the second animal through the second extracorporeal circuit, and where a fourth blood portion passing through the second pores flows through the second bypass and into the first extracorporeal circuit for entering the vascular system of the first animal. One or more of the first bypass and the second bypass may include a pump. One or more of the first bypass and the second bypass may include a flow control device. The system may further include a third extracorporeal circuit including the first filter and the first bypass, where the third extracorporeal circuit is structurally configured to promote movement of blood through the first filter. The third extracorporeal circuit may include a pump. The pump may be disposed along a portion of the third extracorporeal circuit where blood is returned to the first filter from the first bypass. The system may further include a fourth extracorporeal circuit including the second filter and the second bypass, where the fourth extracorporeal circuit is structurally configured to promote movement of blood through the second filter. The fourth extracorporeal circuit may include a pump. The pump may be disposed along a portion of the fourth extracorporeal circuit where blood is returned to the second filter from the second bypass. The filtering circuit may further include a mixing chamber in fluid communication with each of the first filter and the second filter, the mixing chamber structurally configured to receive filtered blood from the first animal and filtered blood from the second animal for mixing within the mixing chamber. An outlet of the mixing chamber may be in fluid communication with one or more of the first extracorporeal circuit and the second extracorporeal circuit for supplying mixed blood to one or more of the first extracorporeal circuit and the second extracorporeal circuit. The system may further include a pump disposed between the outlet of the mixing chamber and one or more of the first extracorporeal circuit and the second extracorporeal circuit. The system may further include a filter disposed between the outlet of the mixing chamber and one or more of the first extracorporeal circuit and the second extracorporeal circuit. The system may further include a flow control device disposed between the outlet of the mixing chamber and one or more of the first extracorporeal circuit and the second extracorporeal circuit. An outlet of the mixing chamber may be in fluid communication with each of the first extracorporeal circuit and the second extracorporeal circuit for supplying mixed blood to each of the first extracorporeal circuit and the second extracorporeal circuit. The mixing chamber may be a tube. The system may further include a third extracorporeal circuit including the first filter and the mixing chamber, the third extracorporeal circuit structurally configured such that filtered blood travels from the first filter into the mixing chamber and mixed blood is returned to the first filter from the mixing chamber. The third extracorporeal circuit may include a pump. The pump may be disposed along a portion of the third extracorporeal circuit through which mixed blood is returned to the first filter from the mixing chamber. The system may further include a fourth extracorporeal circuit including the second filter and the mixing chamber, the fourth extracorporeal circuit structurally configured such that filtered blood travels from the second filter into the mixing chamber and mixed blood is returned to the second filter from the mixing chamber. The fourth extracorporeal circuit may include a pump. The pump may be disposed along a portion of the fourth extracorporeal circuit through which mixed blood is returned to the second filter from the mixing chamber. The first pump may be disposed between the first outlet and the first filter. The first pump may be disposed between the first filter and the first inlet. The system may further include a solution that is present within the first extracorporeal circuit before blood from the first animal traverses through the first extracorporeal circuit. The first filter and the second filter may be the same type of filter. The first filter and the second filter may be different types of filters. The system may further include a balancer in fluid communication with one or more of the first extracorporeal circuit and the second extracorporeal circuit. The pore size may allow for passage of molecules having a molecular weight of between about 70 kilodaltons (kda) and 140 kda.

In an aspect, a parabiotic dialysis system disclosed herein may include: a first extracorporeal circuit, including a first outlet and a first inlet connecting the first extracorporeal circuit to the vascular system of a first animal, and a first pump structurally configured to move blood through the first extracorporeal circuit between the first outlet and the first inlet. The system may further include a second extracorporeal circuit, including a second outlet and a second inlet connecting the second extracorporeal circuit to the vascular system of a second animal, and a second pump structurally configured to move blood through the second extracorporeal circuit between the second outlet and the second inlet. The system may further include a filtering circuit in fluid communication with the first extracorporeal circuit and the second extracorporeal circuit, the filtering circuit including: a first filter including a first semipermeable membrane having first pores, the first filter structurally configured to filter blood from the first animal flowing through the first extracorporeal circuit; and a second filter including a second semipermeable membrane having second pores, the second filter structurally configured to filter blood from the second animal flowing through the second extracorporeal circuit.

These and other features, aspects, and advantages of the present teachings will become better understood with reference to the following description, examples, and appended claims.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

FIG. 5 illustrates a device for parabiotic dialysis, in accordance with a representative embodiment.

FIG. 6 illustrates a cross-sectional view of a device for parabiotic dialysis, in accordance with a representative embodiment.

FIG. 7 illustrates a cross-sectional view of a device for parabiotic dialysis, in accordance with a representative embodiment.

DETAILED DESCRIPTION

Figure 1:
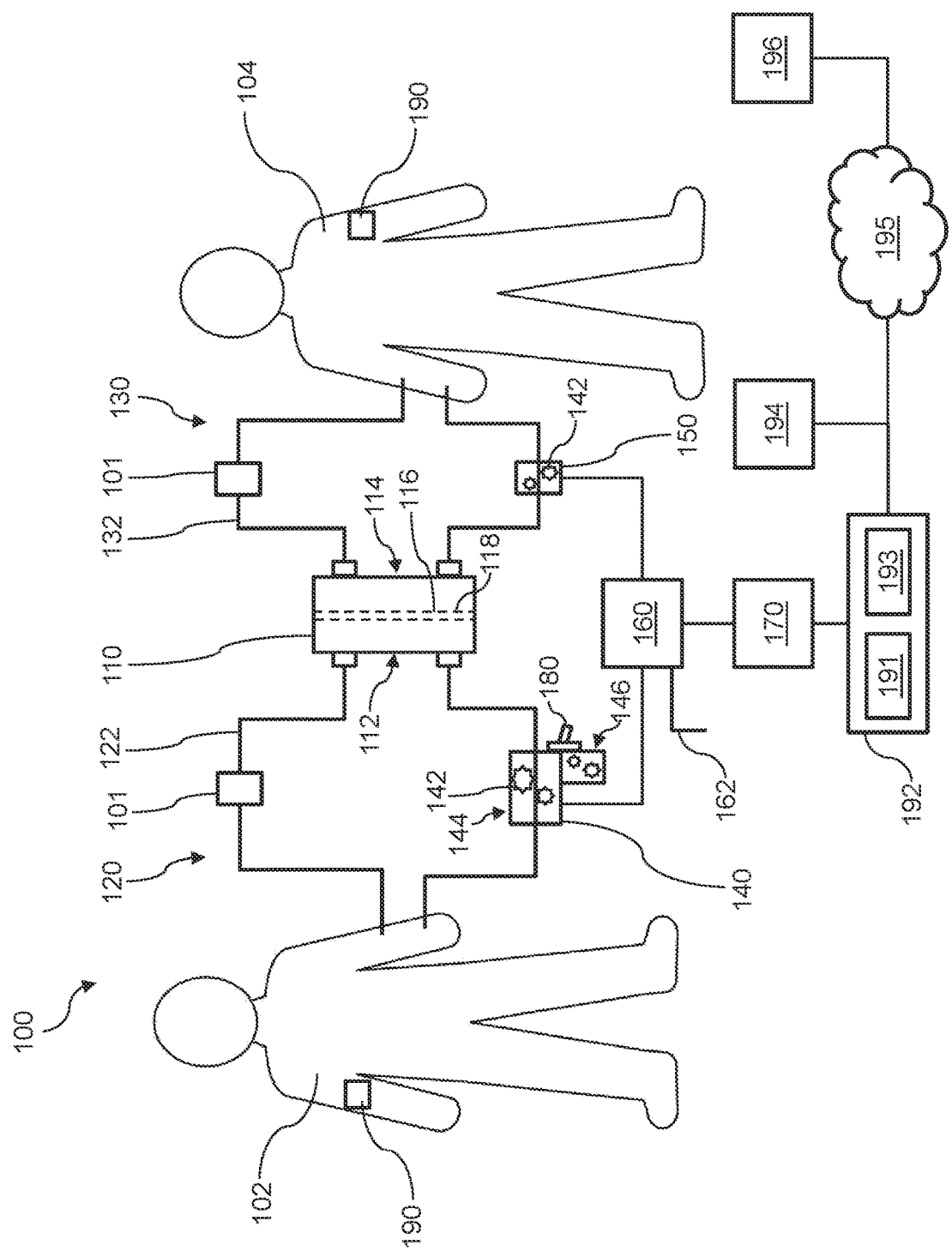
FIG. 1 illustrates a system for parabiotic dialysis, in accordance with a representative embodiment.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless specifically stated to the contrary.

In general, the devices, systems, and methods disclosed herein relate to parabiotic dialysis. That is, the present teachings may include dialysis treatments that are intended to enable dialysis to be available in environments where access is often unavailable. For example, dialysis treatments may be unavailable in environments where access to certain resources (e.g., a reliable power source, fresh clean water, and so on) is limited or unavailable, such as regions with developing or unreliable infrastructures (e.g., third-world countries or economically-challenged areas), undeveloped regions, and disaster-stricken areas (e.g., a developed region affected by a natural disaster, military conflict, or the like that has temporarily disabled its infrastructure). In this manner, certain devices, systems, and methods disclosed herein may be similar to the hemodialysis techniques described in U.S. Pat. No. 10,391,220, the entirety of which is incorporated by reference herein. As described with respect to certain embodiments of U.S. Pat. No. 10,391,220, in contrast to standard hemodialysis, a dialysis patient may not be dialyzed against a circulating dialysate, but instead against the blood of a healthy human donor, where there is a first circuit feeding the blood of a kidney patient through the blood side of a dialyzer, and a second circuit where the blood of a healthy animal is circulated through the dialysate side of the dialyzer.

However, unlike the hemodialysis techniques of U.S. Pat. No. 10,391,220, the present teachings include implementations configured specifically for parabiotic liver dialysis. This may, for example, include parabiotic liver dialysis techniques utilizing a semipermeable membrane having pores with a pore size structurally configured to allow for the passage of albumin therethrough and/or to prevent or minimize the passage of certain other blood components therethrough. Albumin is a protein found in the blood that carries water insoluble substances including toxins, where a healthy liver normally removes such albumin-bound toxins. Thus, in this manner, the present teachings may utilize a more-open membrane (i.e., a membrane with a larger molecular weight cutoff) than that used for kidney dialysis, where this more-open membrane is structurally configured to allow for the passage of albumin therethrough, but small enough to prevent the passage of larger molecules or compounds. For example, in an aspect, the semipermeable membrane may have an average pore size allowing for the passage of molecules having molecular weights between about 70 kilodaltons (kDa) and 140 kDa. By way of further example, in an otherwise relatively open embodiment, the semipermeable membrane may prevent passage of red blood cells to make the concept independent of blood type compatibility where non-compatible blood types could cause severe immune reactions. It may further be desirable to exclude passage of low density lipoprotein having a size of about 2700 kDa, in particular when an animal using techniques of the present teachings suffers from relatively high cholesterol levels. It may further be desirable to exclude the passage of immunoglobulin type M (IgM) having a size of about 950 kDa, which forms a first line of defense of the immune system to compounds foreign to the body, and thus the passage of IgM may cause adverse immune reactions. It may or may not be desirable to exclude the passage of fibrinogen, which forms part of the blood coagulation system. Whether the passage of fibrinogen is desired may depend both on the fibrinogen levels of a patient using techniques of the present teachings and the overall thrombogenic status of the patient. It further may or may not be desirable to exclude the passage of immunoglobulin type G (IgG) having a size of about 150 kDa. This is because a transfer of IgG between animals using the present teachings may on one hand support the immune system of a patient, but on the other hand it may cause adverse immune reactions due to incompatibilities. It will therefore likely depend on individual case specifics (e.g., patient specifics) whether the transfer of IgG is desirable. It may be further desirable to exclude the passage of endotoxins having a size of about 100 kDa. However, because the level of endotoxins in the blood of a healthy animal is expected to be relatively low, and a transfer of a limited amount of endotoxins from a patient to a healthy animal is of relatively little risk, the passage of endotoxins may be acceptable if a transfer of larger molecules such as IgG is desired.

It will be understood that, unless explicitly stated to the contrary or otherwise clear from the context, when it is stated herein that a substance is "allowed to pass" (or the like) through a membrane as described herein, this shall mean that at least about 10% or more—and usually much more, such as more than 25%, more than 50%, or more than 65%—of that substance will pass through the membrane in the particular environment that the membrane is contemplated for use (e.g., when in blood). Stated otherwise, a substance that is "allowed to pass" (or the like) through a membrane as described herein will not be a substance where only about 10% or less of that substance will be passing through the membrane in the particular environment that the membrane is contemplated for use (e.g., when in blood). It will also be generally understood that when it is stated herein that a substance is "prevented from passage" (or the like) through a membrane as described herein, this shall mean that only about 10% or less of that substance will pass through the membrane in the particular environment that the membrane is contemplated for use (e.g., when in blood). Similarly, it will be understood that, unless explicitly stated to the contrary or otherwise clear from the content, when it is stated herein that a substance is "allowed to pass" (or the like) through a membrane as described herein, this shall mean that at least a plurality of—e.g., most, if not all—pores in the membrane are sized larger than the average size of that particular substance, thereby allowing the substance to pass through these pores in the membrane. However, it will be understood that when it is stated herein that a substance is "allowed to pass" (or the like) through a membrane as described herein, this shall not necessarily mean that 100% of that substance will traverse through pores of the membrane, and it will similarly be understood that when it is stated herein that a substance is "prevented from passage" (or the like) through a membrane as described herein, this shall not necessarily mean that 100% of that substance will not pass through pores of the membrane—i.e., these statements are not to be interpreted as absolute statements unless explicitly stated to the contrary or otherwise clear from the context.

The appropriate membranes to be used in the context of the present teachings may thus be defined by their molecular weight cut-off (MWCO). The MWCO is generally defined as a sieving coefficient of 0.1 for a particular substance, meaning that only about 10% of a substance will pass through the membrane. It will also be understood that the value of a sieving coefficient may vary depending how it is measured—e.g., whether the MWCO is measured in blood or in an aqueous solution. When measured in blood, the MWCO of a membranes may be closely related to the compound desirous to be excluded from passage. For example, if only red blood cells are desirous for exclusion from passage, any plasma filter available on the market would likely suffice; if LDL is desirous for exclusion from passage, the MWCO as measured in blood should be less than 2700 kDa; if IgM is desirous for exclusion from passage, the MWCO as measured in blood should be less than 950 kDa; if fibrinogen is desirous for exclusion from passage, the MWCO as measured in blood should be less than 340 kDa; if IgG is desirous for exclusion from passage, the MWCO as measured in blood should be less than 150 kDa; if endotoxins are desirous for exclusion from passage, the MWCO as measured in blood should be less than 100 kDa; and, to allow for the passage of albumin for using the present teachings in a liver dialysis technique, the MWCO as measured in blood should be more than 66 kDa. Thus, in an aspect, the lower limit for the MWCO as measured in blood for a membrane used in the present teachings may be about 66 kDa to promote the passage of albumin therethrough, and the upper limit for the MWCO may depend on other substances, molecules, or compounds that are desirous for exclusion from passage (e.g., an upper limit for the MWCO as measured in blood may be about 150 kDa if IgG is desirous for exclusion from passage, an upper limit for the MWCO as measured in blood may be about 340 kDa if fibrinogen is desirous for exclusion from passage, an upper limit for the MWCO as measured in blood may be about 950 kDa if IgM is desirous for exclusion from passage, and an upper limit for the MWCO as measured in blood may be about 2700 kDa if LDL is desirous for exclusion from passage). Thus, many ranges of MWCOs for semipermeable membranes are contemplated herein, although most will fall within the range of about 66 kDa on the low end and about 2700 kDa on the high end. Other MWCOs are also or instead possible.

A lower limit for the MWCO as measured in blood of about 66 kDa to about 70 kDa may translate to a sieving coefficient in blood for albumin of greater than about 0.2—it will be understood that higher sieving coefficients in blood for albumin are also or instead possible and may be desirous such as 0.5 or greater, and 0.75 or greater. For example, if the lower limit for the MWCO as measured in blood is about 85 kDa, this can result in a sieving coefficient in blood for albumin of greater than about 0.5; and if the lower limit for the MWCO as measured in blood is about 150 kDa, this can result in a sieving coefficient in blood for albumin of greater than about 0.75. Further, the aforementioned examples of upper limits for the MWCO as measured in blood may translate to a sieving coefficient in blood of less than about 0.1 for the particular substance desirous for exclusion from passage.

By way of example and not of limitation, two example filters—Filter 1 and Filter 2—that have suitable filtering characteristics for certain implementations of the present teachings are included in Table 1 below. As discussed herein, the sieving coefficient (SC) retention onset (RO) defines the start of the sieving curve of a membrane, where the membrane is generally not a significant barrier for molecules with a molecular weight lower than this value. The RO is typically defined at a SC of 0.9 for a given molecule or molecular weight. Further, retention of a molecule generally starts at the sieving coefficient cutoff (CO), where the CO is typically defined at a SC of 0.1 for a given molecule or molecular weight.

TABLE 1

| | Area [m²] | SC Albumin (64 kDa) | SC Fibrinogen (340 kDa) | SC LDL (2-3 MDa) | DexSC RO (0.9) | DexSC CO (0.1) |
|---|---|---|---|---|---|---|
| Filter 1 | 2.0 | >0.75 | | <0.09 | 24 kDa | 528 kDa |
| Filter 2 | 1.0 | >0.6 | >0.1 | | 23 kDa | 340 kDa |

The measuring of the SC for dextran ("DexSC" in Table 1) is described by way of example in U.S. Patent. App. Pub. No. 2019/0381462 to Keller, et al., the entire content of which is hereby incorporated by reference herein. One may observe that the measurement of the SC of fibrinogen in blood and the MWCO of 340 kDa for dextran in water may be surprisingly close, where a SC that is lower in blood than in an aqueous solution may have been expected because protein deposits on the membrane when measured in blood could be expected to decrease pore size. This may suggest that, in contrast with typical dialysis membranes, although protein deposits may affect the SC for membranes with a larger pore size, it may be to a lesser extent. In other words, for membranes with larger pore size, SC measurements in blood and in an aqueous solution may yield similar results.

In Table 1 above, Filter 1 may correspond to a MONET® filter and Filter 2 may correspond to an ALBUFLOW® filter, where MONET® and ALBUFLOW® are registered trademarks of Fresenius Medical Care.

It will be understood that appropriate membranes to be used in the context of the present teachings may also or instead be defined by an average pore size as measured in nanometers (nm). For example, a lower limit for the average pore size of a membrane used herein that can still allow for the passage of albumin therethrough may be about 4 nm, about 6 nm, about 7 nm, about 8 nm, or greater. Similarly, the upper limit for the average pore size of a membrane used herein may depend upon a substance desirous for exclusion from passage. For example, an upper limit for the average pore size of a membrane used herein that can prevent the passage of IgG therethrough may be about 5 nm (it is noted that this upper limit may be in conflict with a lower limit for allowing albumin passage, and thus may be increased for aspects of the present teachings); an upper limit for the average pore size of a membrane used herein that can prevent the passage of fibrinogen therethrough may be about 7 nm; an upper limit for the average pore size of a membrane used herein that can prevent the passage of IgM therethrough may be about 10 nm, and an upper limit for the average pore size of a membrane used herein that can prevent the passage of LDL therethrough may be about 14 nm. In this manner, many ranges for average pore size for semipermeable membranes are contemplated herein, although most will fall within the range of about 5 nm on the low end and about 14 nm on the high end. Other pore sizes are also or instead possible.

Thus, it will be understood that a membrane of the present teachings may have a MWCO (as measured in blood with a sieving coefficient of 0.1) that is greater than 66 kDa. Also or instead, a membrane of the present teachings may have a MWCO (as measured in blood with a sieving coefficient of 0.1) that is less than 2700 kDa. More particularly, a membrane of the present teachings may have a MWCO (as measured in blood with a sieving coefficient of 0.1) that is less than 340 kDa. More particularly, a membrane of the present teachings may have a MWCO (as measured in blood with a sieving coefficient of 0.1) that is less than 150 kDa. Also or instead, a membrane of the present teachings may have a sieving coefficient in blood for albumin that is greater than 0.2. Also or instead, a membrane of the present teachings may have an average pore size that is greater than 4 nm. Also or instead, a membrane of the present teachings may have an upper limit of the average pore size that is less than 14 nm, or in certain aspects, less than 5 nm. In some implementations, the average pore size for a membrane of the present teachings is between 5 nm and 14 nm. Also or instead, a membrane of the present teachings may be structurally configured to allow for the passage of albumin but to prevent the passage of one or more of red blood cells, LDL, IgM, fibrinogen, IgG, and endotoxins.

In general, it may be desirable for the membrane of the present teachings to have a relatively high water permeability because a higher water permeability increases the convective flow across the membrane and therefore promotes an increased transfer of compounds desired to be transferred. The water permeability can be measured by the coefficient for ultrafiltration (KUF). This is described in, for example, U.S. Patent Application Publication No. 2019/0381462, which is hereby incorporated by reference herein in its entirety. By way of example, a lower limit for water permeability (units=ml/(m²*h*mmHg)) for a membrane configured to allow albumin to pass may be about 500, or about 1000, or about 1500; and an upper limit for water permeability (units=ml/(m²*h*mmHg)) for a membrane may be about 6000, or about 4500.

Table 2 below shows ultrafiltration measurements for example filters that can be used in certain implementations of the present teachings—Filter 1 and Filter 2 from Table 1 above, and an additional example filter, Filter 3, which may correspond to the PlasmaFlux P2 Dry Filter from Fresenius Medical Care.

TABLE 2

| | Area [m²] | UF SOP [mL/h/mmHg/m2] | UF Membrane [mL/h/mmHg/m2] |
|---|---|---|---|
| Filter 1 | 2.0 | 600 | 1700 |
| Filter 2 | 1.0 | 900 | 1700 |
| Filter 3 | 0.6 | 2900 | 30000 |

The following formulas can be used to find information similar to that shown in Table 2: Stokes radius [nm] =0.04456*(dextran mol weight)$^{0.43821}$ (see J. Brandrup, E. H. Immergut "Polymer Handbook" (1989), pp. 112 to 113, John Wiley & Sons, Inc., and Artificial Organs, V13, No. 6 (1984) pp. 23 to 30, where each is incorporated by reference herein); Stokes radius [Å]=(mol weight)$^{1/3}$—which is an estimate for spherical polymers; and the standards for calibrating analytical gel filtration as described in La Verde, V., Dominici, P. and Astegno, A. (2017), Determination of Hydrodynamic Radius of Proteins by Size Exclusion Chromatography. Bio-protocol 7(8): e2230, incorporated by reference herein. It can also be helpful to review information on Stokes radius and the relation to molecular weight in general, and dextran in particular. One can also look to Vanholder, Raymond, et al, "Review on Uremic Toxins: Classification, Concentration, and Interindividual Variability," Kidney International, Vol. 63 (2003), pp. 1934-1943, which is incorporated by reference herein.

The setup for the ultrafiltration measurements of Table 2 may work relatively well with typical dialysis membranes, but there can be a flaw that becomes more salient the more permeable the membrane becomes. This flaw may be that the pressure drop across the housing and connecting lines is not taken into account in these measurements. In a dialysis filter, the pressure drop across the membrane may be so high that this type of error is small; however, with a highly permeable filter, the reverse can be true. Thus, one can obtain significantly different values depending on the housing in which a membrane is installed. In the test setup used for creating Table 2, both values are determined, but the official value is the first one listed, where the second value may only be used for estimating the error (i.e., it can represent the ultrafiltration of the membrane without a housing).

The use of a semipermeable membrane that allows for the passage of albumin may be contrary to, and highly distinguishable from, many past teachings related to hemodialysis and parabiotic dialysis generally, where membranes and filters typically have a molecular weight cutoff that prevents the passage of albumin (66 kDa) therethrough. In fact, for traditional dialysis, a non-trivial consideration in choosing the molecular weight cutoff of a dialysis membrane usually includes the avoidance of albumin loss, since albumin is not substituted by standard dialysate.

Some technical advantages of using a semipermeable membrane with a higher molecular weight cutoff than standard hemodialysis membranes may include one or more of the following: the fluid exchange between a patient and a healthy animal may be increased due to the increased flux rate of the membrane (e.g., which can in turn provide greater pressure potential). By way of example, using a semipermeable membrane having an enhanced water permeability may be desirous. Thus, in general, having increased flux for a membrane can increase backfiltration and therefore convective transport, which may permit relatively higher molecular weight particles to pass through the membrane), thereby improving efficiency of a dialysis treatment; and because some uremic toxins are albumin bound, these toxins can be difficult to remove in a standard dialysis treatment, but using a semipermeable membrane with a higher molecular weight cutoff can promote the transfer of bound uremic toxins from a patient to a healthy animal that can metabolize these toxins—stated otherwise, a semipermeable membrane with a higher molecular weight cutoff can allow for the exchange and metabolization of albumin-bound toxins. To this end, the use of a semipermeable membrane with a higher molecular weight cutoff can allow for an efficient therapy for acute deterioration of liver function, e.g., for patients with acute liver failure or a rapid decline due to chronic liver failure. The present teachings can therefore address an unmet medical need since most current liver support systems show a relatively low efficacy.

Thus, the devices, systems, and methods disclosed herein may be structurally configured for performing liver dialysis. Generally, liver dialysis is a detoxification treatment for patients with liver failure or other various liver disorders (e.g., acute liver failure, reduced liver function, decompensated chronic liver disease, hepatorenal syndrome, liver failure after liver surgery, secondary liver failure, multi organ failure, intractable pruritus in cholestasis, or the like)—where an animal having one or more of these conditions (or related conditions) may generally be referred to herein as a "liver patient," and where an animal having relatively normal liver function (or a liver function that is capable of supplementing the liver function of the liver patient) may generally be referred to herein as a "healthy animal." Liver dialysis may also or instead be used as a short-term treatment option ("bridging") before transplantation.

Multiple solutes accumulate in blood as the excretory and metabolic function of a failing liver declines. Many of these substances play a critical role in the pathophysiology of hepatic failure. A significant portion of these toxins are albumin-bound (e.g., bilirubin, bile acids, metabolites of aromatic amino acids, medium-chain fatty acids, and cytokines). Thus, by allowing for the passage of albumin between a liver patient and a healthy animal as contemplated herein, albumin that is bound with these toxins in the liver patient can pass to the healthy animal, where the healthy animal's liver can metabolize these toxins. Also, or instead, toxin-free albumin may pass from the healthy animal to the liver patient using implementations described herein. That is, because the healthy animal's blood will usually include albumin in normal levels, the present teachings can result in a diffusive exchange between the liver patient's and the healthy animal's blood in which the albumin levels converge. Consequently, there may be little to no risk of a depletion of albumin in the liver patient's blood using implementations described herein. Moreover, patient's experiencing liver failure typically have lower albumin levels compared to healthy individuals, so albumin may flow from the healthy animal to the liver patient, where the healthy animal should be able to generate albumin at a sufficient rate to cover the transfer or loss to the liver patient.

The present teachings may represent an improvement over existing techniques in the following manner. The present teachings may represent an improvement over standard dialysis membranes, which typically have a molecular weight cutoff that prevents the passage of albumin (e.g., which may be around 66 kDa) as discussed above. While some parabiotic teachings have disclosed using membranes with smaller molecular weight cutoffs (e.g., around 5-10 kDa), these disclosures generally teach away from using more open membranes (e.g., to prevent the passage and loss of albumin). In contrast, the present teachings may utilize a more open membrane (having a molecular weight cutoff of about 70 kDa-140 kDa, or larger) to enable the passage of albumin for the metabolizing of toxins by a healthy animal that receives the albumin-bound toxins from a liver patient or the like. Moreover, although other systems may include albumin exchange (e.g., for the treatment of Alzheimer's disease or liver failure), these therapies are usually similar to plasmapheresis (for a total plasma exchange), which also exchanges larger molecules such as antibodies and fibrinogen. In contrast, the present teachings may prevent the exchange of such larger molecules to mitigate the risk of infections and immune reactions. Further, existing liver support systems may not utilize a healthy animal to clear toxins from a liver patient's blood. Instead, existing liver support systems may be based on the dialysis of blood against an albumin-containing dialysate solution, where the albumin does not pass through a membrane, but rather the albumin-bound toxins transfer from the patient's albumin to the dialysate albumin through the membrane. In this manner, disclosed parabiotic liver support treatments and systems may provide improved efficacy and accessibility over existing treatments options.

The devices, systems, and methods disclosed herein may also relate to performing dialysis with limited resources such as environments and settings with limited or no availability or access to fresh water or energy (e.g., electricity) to run pumps and other dialysis equipment and components. For example, the present teachings may be used in undeveloped, underdeveloped, or disaster-stricken regions for providing dialysis to patients. Also, or instead, the present teachings may otherwise be used by patients outside of a treatment facility, e.g., when at home or when traveling.

To this end, the present teachings may include a dialysis system that does not require access to grid power to run pumps and other components of the system. Also, or instead, the present teachings may include a system where dialysis is performed using a healthy animal (e.g., a person with normal liver function) to help remove harmful solutes from, and provide helpful solutes to, a liver patient. In this manner, dialysate, filters, or absorbers that would be used in a traditional treatment may be replaced by the blood of a healthy animal, e.g., without a need for a fresh water source. The healthy animal's blood may thus receive albumin-bound toxins from the liver patient's blood, which can then be processed by the healthy animal via its relatively normal liver function. Thus, the healthy animal is "virtually donating" its liver function to the liver patient for the duration of the treatment. Also or instead, toxin-free albumin may pass from the healthy animal to the liver patient using the present teachings.

The present teachings may thus include a traditional dialysis configuration (e.g., using a dialyzer connected to a patient in a relatively conventional manner), however, the present teachings may include using a healthy animal with adequate liver function to eventually remove harmful solutes (e.g., albumin-bound toxins) and to eventually provide helpful solutes to a liver patient (e.g., toxin-free albumin). That is, the dialyzer may be connected to the healthy animal's vascular system using the dialysate ports of the dialyzer. In this manner, convective/diffusive processes may occur across a membrane of the dialyzer—albumin may migrate across the membrane from the liver patient to the healthy animal. Moreover, filtration can be accomplished by establishing a pressure gradient between the two sides of the dialyzer. The albumin-bound toxins may then be cleared from the healthy animal via its normal liver function.

Thus, implementations described herein may include a treatment option for the support of liver function. In particular, implementations described herein may include a treatment option with improved efficacy, where the treatment may be more readily available in environments where access to other existing treatment options may not be available.

It will be understood that implementations described herein could be used for extracorporeal liver support therapy or for conventional dialysis alone. Further, implementations described herein may be used to remove protein-bound and water-soluble toxins from the blood, including for example, ammonia, urea, aromatic amino acids, manganese, benzodiazepine-like substances, and the like.

The present teachings further include various safety measures for parabiotic dialysis systems—e.g., the hemodialysis systems and techniques described in U.S. Pat. No. 10,391, 220, and the parabiotic liver dialysis systems and techniques described herein. Such safety measures may be desirous because such parabiotic dialysis systems and techniques may have a potential for misuse, exploitation, and coercion, particularly in developing or economically-challenged regions. By way of example, and as explained in more detail herein, to prevent or mitigate these risks, a biometric verification system may be used as a safeguard. In this manner, a patient and a healthy animal may be planned or prescribed matches, where their identity must be verified, e.g., using a biometric identifier, fingerprint identification, retinal scanning, voice recognition, combinations thereof, and the like. These identifiers may be compared with a treatment prescription file, e.g., stored in a cloud-based database (or another database). In this manner, systems can be configured such that verification is required before treatment is allowed to begin or to continue (if started). In other words, in some implementations, a treatment can only be started if biometric identification of the patient and the healthy animal is verified (e.g., concurrently verified). Moreover, in some implementations, verification could be routinely repeated throughout a treatment. Such a system could prevent an unprescribed healthy animal from unknowingly volunteering or being forced to provide treatment for the patient. It is envisioned that a prescriber could prescribe or match one or more healthy animals for a patient.

FIG. 1 illustrates a system for parabiotic dialysis, in accordance with a representative embodiment. As described herein, the system 100 may be used to perform liver dialysis, and/or other forms of dialysis such as hemodialysis, when there is limited (or zero) access to grid power or fresh water. In this manner, the system 100 may be used as an emergency replacement to other dialysis treatments or systems. The system 100 may generally include a first animal (e.g., a liver patient 102 as shown in the figure), a second animal (e.g., a healthy animal 104 as shown in the figure), a device 110 structurally configured for the transfer of one or more molecules or solutes therethrough, a first extracorporeal circuit 120, a second extracorporeal circuit 130, one or more pumps (e.g., a first pump 140 and a second pump 150 as shown in the figure), one or more drivers 160 for driving the one or more pumps, an energy source 170 for supplying energy to one or more components of the system 100, one or more sensors 190, a controller 192, a biometric verification system 194, a data network 195, and one or more external resources 196.

The liver patient 102 may include a human or other animal that has liver failure or other various liver disorders such as acute liver failure, decompensated chronic liver disease, hepatorenal syndrome, liver failure after liver surgery, secondary liver failure, multi organ failure, intractable pruritus in cholestasis, and the like. The liver patient 102 may also or instead be a pre-transplant patient, where the system 100 is used as a short-term treatment option before transplantation. Although primarily discussed in the context of liver dialysis, the system 100 may also or instead be used for (or adapted for use for) other dialysis techniques and similar. Thus, the liver patient 102 may also or instead include a human that has kidney disease (e.g., acute or chronic kidney disease), or has experienced a form of kidney failure, thus needing hemodialysis treatments. Similarly, and unless explicitly stated to the contrary or otherwise clear from the context, when the present disclosure references liver dialysis, it will be understood that other forms of dialysis may be conducted using the system 100.

The healthy animal 104 may preferably include a human. The healthy animal 104 may alternatively include a non-human, e.g., a horse, a cow, a sheep, and so on. It will be understood that, although the use of a human as the healthy animal 104 may be preferred, a non-human animal may be preferable to foregoing certain dialysis treatments entirely. In particular, some blood borne pathogens that are typically found only in animals (e.g., prions that can cause bovine spongiform encephalopathy (BSE), commonly known as mad cow disease) are only about 10-nm in diameter, which is small enough to cross a typical dialyzer membrane. The risk of exposure to these or other blood borne pathogens may be weighed against the risk of foregoing dialysis entirely, on a case by case basis.

The term "healthy" as used herein when describing the healthy animal 104 shall mean that the animal has apparently normal liver function, where "normal" will be understood to include liver function that does not need supplementation or treatment via liver dialysis or the like. For example, if described as "healthy" or "normal" herein, this shall mean that the subject being described has indicators of liver function, such as coagulation tests and other lab parameters, that are within a normal, widely-acceptable range. The term "healthy" when describing the healthy animal 104 may also or instead include an animal that has greater liver function than the liver patient 102.

In the context of the present teachings, the liver patient 102 can be thought of as simply a first animal, and the healthy animal 104 can be thought of as simply a second animal. The first animal may be any animal where it is desirous to perform liver dialysis on that animal's blood and return the processed blood to the animal—e.g., the first animal may have a liver disorder such as one or more of acute liver failure, decompensated chronic liver disease, hepatorenal syndrome, liver failure after liver surgery, secondary liver failure, multi-organ failure, hepatic encephalopathy, and cholestasis. The first animal may also or instead have jaundice—e.g., the first animal may be a human infant with jaundice. The second animal may be any animal whose blood contains molecules that are desirous for transfer into the blood of the first animal, and/or any animal that has a liver function such that molecules transferred from the blood of the first animal will not significantly harm the second animal (e.g., the molecules may be cleared from the second animal via its normal liver function, such as where dilution of the molecules will occur in the second animal without significant adverse effects). Stated otherwise, blood from one or more of the first animal and the second animal may contain molecules that are desirous for transfer into blood of the other one of the first animal and the second animal. Thus, generally, the present teachings may use two living animals that form parts of the first extracorporeal circuit 120 and the second extracorporeal circuit 130 in the system 100.

The device 110 shown in the figure may be a dialyzer, which may be any as known in the art, e.g., a standard "off-the-shelf" dialyzer. For example, the device 110 may include one or more of a hollow-fiber dialyzer and a plate dialyzer. The device 110 may also or instead merely define a housing for the placement of a membrane or filter that is structurally configured to permit the passage of one or more molecules therethrough (e.g., for diffusion). Thus, in general, the device 110 may include a filter for parabiotic dialysis, such as any of the filters, membranes, and absorbers described herein.

The device 110 may thus include a semipermeable membrane 116. The semipermeable membrane 116 may include pores 118 with a pore size structurally configured to allow for the passage of specific molecules (e.g., albumin) therethrough and/or pores 118 with a pore size structurally configured to prevent the passage of other molecules (e.g., antibodies) therethrough. To this end, the semipermeable membrane 116 may have pores 118 with an average pore size that allows for the passage of molecules therethrough having a molecular weight of between about 70 kDa and 140 kDa (or larger)—such that the average pore size may allow for the passage of albumin therethrough. For example, in certain implementations, the semipermeable membrane 116 may lack any pores 118 with a pore size that permits the passage of molecules smaller than 70 kDa and larger than 140 kDa. Stated otherwise, the molecular weight cutoff of the semipermeable membrane 116 may be between about 70 kDa and 140 kDa. In certain implementations, the pore size of the pores 118 of the semipermeable membrane 116 is structurally configured to prevent passage of fibrinogen therethrough. In certain implementations, the pore size for pores 118 of the semipermeable membrane 116 is structurally configured to prevent passage of immunogenic substances therethrough. In certain implementations, the pore size for pores 118 of the semipermeable membrane 116 is structurally configured to prevent passage of pathogens therethrough—e.g., where the pathogens prevented from passing through the semipermeable membrane 116 include one or more of a virus and bacteria. It will be understood that other pore sizes are also or instead possible. Regardless, in general, the device 110 may include a semipermeable membrane 116 for the passage of one or more molecules therethrough (e.g., for diffusion). In certain implementations, the semipermeable membrane 116 includes one or more of a hollow-fiber (or a grouping of hollow fibers) and a plate.

It will be understood that, although an aspect of a semipermeable membrane 116 is described herein as having pores 118 with an average pore size that allows for the passage of molecules therethrough having a molecular weight of between about 70 kDa and 140 kDa, and an aspect of a semipermeable membrane 116 is described herein that allows for the passage of at least molecules therethrough having the molecular weight of albumin, a semipermeable membrane 116 contemplated herein may have a higher molecular weight cutoff. It will also be understood that the cutoff of the semipermeable membrane 116 depends on which components of blood are desired to be excluded. For example, if IgG antibodies are to be excluded, a molecular weight cutoff of 140 kDa may be contemplated for the semipermeable membrane 116. However, this may also depend on the type of measurement technique, where generally the MWCOs described herein are in the context of blood, as the semipermeable membrane 116 may be used to filter blood in most embodiments. By way of example, a semipermeable membrane 116 contemplated herein may have a relatively high molecular weight cutoff, i.e., one that is greater than about 140 kDa. For example, because in vivo protein deposits on the semipermeable membrane 116 can build a "secondary membrane" that essentially closes-up pores 118, the semipermeable membrane 116 may have pores 118 that allow (at least initially) molecules to pass through that have a higher molecular weight than about 140 kDa. This effect may account for the difference of the cutoff value when measured in water where no protein deposits occur, or in blood where the secondary membrane is built over time during treatment. In other words, the semipermeable membrane 116 may be designed to account for biological material build-up on a surface thereof (during use) that can affect its porosity. In this manner, an error tolerance or the like may be accounted for when determining the pore sizes of the semipermeable membrane 116. Regardless, in an embodiment described herein, the effective molecular weight cutoff of the semipermeable membrane 116 during use thereof may be above 70 kDa, such that the semipermeable membrane 116 allows for the passage of albumin therethrough. The effective MWCO may be measured in blood according to protocol in the following paragraph.

The semipermeable membrane 116 is primed with an isotonic saline solution at a temperature of about 37° C. About 1 liter of a blood sample prepared for the measurement has a hematocrit of about 40% and a protein content of about 6% by weight. The blood sample is circulated inside the semipermeable membrane 116 for about 10 minutes to prepare the measurement. For the measurement, the system is operated in a filtration only mode at a blood flow of about 200 ml/min and a filtrate flow of about 40 ml/min, and a sample of the filtrate is taken after about 30 minutes and centrifuged at about 4000 rpm. The sieving coefficient of a component is calculated as the amount present in the filtrate sample divided by the concentration in the blood sample. All amounts may be measured at least in triplicate by an analytic device (e.g., a Cobas Integra® 400 Plus by the Roche Group).

The semipermeable membrane 116 may have a water permeability as described above. For example, the semipermeable membrane 116 may have a lower limit for water permeability (units=ml/(m$^2$*h*mmHg)) of about 500, or about 1000, or about 1500; and an upper limit for water permeability (units=ml/(m$^2$*h*mmHg)) may be about 6000, or about 4500. Similarly, pore sizes for the pores 118 of the semipermeable membrane 116 may be the same or similar to the pore sizes mentioned above. By way of example, a lower limit for the average pore size of a membrane used herein that can still allow for the passage of albumin therethrough may be about 4 nm, about 6 nm, about 7 nm, about 8 nm, or greater.

The present teachings encompass embodiments where the blood of a first animal (e.g., a liver patient or a kidney patient) is dialyzed directly with the blood of a relatively healthy animal. In such embodiments, blood may be present on both sides of the semipermeable membrane 116. For such embodiments, it may be preferred that the outer surface of the semipermeable membrane 116 has a similar average pore size, rate of pore area, and average pore area as the inner surface. It is noted that techniques for measuring average pore size, rate of pore area, and average pore area are described in European Patent Publication No. EP1634610A1, which is incorporated by reference herein in its entirety. In hemodialysis, where blood is dialyzed against an aqueous solution, asymmetric membranes are often used. Such membranes may have relatively small pore sizes towards the inner membrane surface and larger pore sizes towards the outer surface membrane. When dialyzing against blood, such a design may, however, be disadvantageous since blood components and proteins may enter larger pores on the outer surface and clot the inside of the membrane. Therefore, for such cases, a semipermeable membrane 116 having an outer surface that does not allow for the passage of particles larger than the size of particles which pass the inner membrane surface may be preferred. For example, the average pore size, rate of pore area, and average pore area may not differ more than 80%, or more preferably 50%, between the inner membrane surface and the outer membrane surface of the semipermeable membrane 116. In a preferred embodiment, the semipermeable membrane 116 is a symmetric membrane.

A semipermeable membrane 116 described herein may thus be structurally configured to allow for the passage of albumin therethrough and/or to prevent the passage of larger blood components, such as antibodies therethrough. However, it will be understood that a semipermeable membrane 116 described herein may have non-homogenous pore sizes resulting in a sieving coefficient curve. Thus, there may not be a hard cutoff in allowing or preventing the passage of certain molecules using the semipermeable membrane 116, but rather the MWCO is defined as a sieving coefficient of 0.1 for a particular substance.

In certain implementations, the semipermeable membrane 116 may be structurally configured to allow for the passage of antibodies therethrough, or at least the semipermeable membrane 116 may not prevent the passage of all antibodies therethrough. For example, in some instances, the passing of antibodies and fibrinogen may not cause major problems for patients, but instead may even be helpful. Therefore, the semipermeable membrane 116 may be structurally configured to have pores 118 that are sized and shaped to permit a certain amount of antibodies and fibrinogen to pass through. However, a semipermeable membrane 116 restricting the passage of IgG antibodies may still be a preferred embodiment.

The semipermeable membrane 116 may be similar to the membranes described in European Patent Publication No. EP1547628 entitled "Plasma Purification Membrane and Plasma Purification System," which is incorporated by reference herein in its entirety, and where it is noted that the membranes described in the foregoing appear to be described and configured for use for different purposes than the techniques described herein.

The device 110 may include a first side 112 and a second side 114. The semipermeable membrane 116 may be disposed between the first side 112 and the second side 114, e.g., to allow for the passage of one or more molecules (e.g., albumin-toxin bound or clean) between the first side 112 and the second side 114. The direction of transfer of the molecules between the first side 112 and the second side 114 may be controllable, e.g., via an establishment of a pressure gradient as described herein or through other means. For example, the transfer of the molecules between the first side 112 and the second side 114 may include an exchange of molecules from each side (i.e., each side receiving molecules from the other side), or solely an exchange of molecules from one side to another side (i.e., where only one side transfers molecules to the other side without receiving molecules from the other side). Also, or instead, certain molecules may be permitted for transfer between the first side 112 and the second side 114 (e.g., in a certain direction), while other molecules are blocked from such transfer.

The first side 112 may be associated with a first animal, who may be the liver patient 102. The second side 114 may be associated with a second animal, who may be the healthy animal 104. Thus, thinking of the device 110 as a dialyzer, the first side 112 can be thought of as the "blood side" of the device 110, and the second side 114 can be thought of as the "dialysate side" of the device 110. The term "dialysate side" will be understood to be a term of convenience used consistently with standard terminology, and does not indicate an intended use. In particular, this document may make reference to a "dialysate side" for a device 110, even when blood of a healthy animal 104 (and not dialysate) is flowing therethrough.

The first extracorporeal circuit 120 may include one or more first fluid lines and/or first fluid connectors 122 structurally configured to connect the first side 112 of the device 110 to the vascular system of a first animal (e.g., the liver patient 102 as shown in the figure). In general, the first extracorporeal circuit 120 may provide a fluid path for drawing blood from the liver patient 102 through the device 110 and back into the vascular system of the liver patient 102 thereby providing processed blood to the liver patient 102. Other than the semipermeable membrane 116 within the device 110 (and/or other filters, absorption elements, and the like), the first extracorporeal circuit 120 may be isolated from the second extracorporeal circuit 130 in the system 100.

The first fluid lines and/or first fluid connectors 122 may include tubing such as intravenous (IV) tubing made from any suitable material, including without limitation, one or more of polypropylene, nylon, dynaflex, and the like. The first fluid lines and/or first fluid connectors 122, or generally the first extracorporeal circuit 120, may also or instead include devices or components used to gain access to the blood of the liver patient 102 for liver dialysis, including without limitation, one or more of an IV catheter, a synthetic graft, and the like.

The second extracorporeal circuit 130 may include one or more second fluid connectors 132 for connecting the second side 114 of the device 110 to the vascular system of a second animal (e.g., the healthy animal 104 as shown in the figure). In general, the second extracorporeal circuit 130 may provide a fluid path for drawing blood from the healthy animal 104 through the device 110 and back into the vascular system of the healthy animal 104. In this manner, the blood from the healthy animal 104 may act in the role of dialysate or an absorber, i.e., where the blood from the healthy animal 104 receives toxins from the blood of the liver patient 102 during a liver dialysis treatment using the system 100 (e.g., toxins that are bound to albumin that are transferred from the blood of the liver patient 102 through the pores 118 of the semipermeable membrane 116 and into the blood of the healthy animal 104). In other words, one or more molecules may be moved to or from the second extracorporeal circuit 130. These molecules may include unwanted or harmful molecules—albumin-bound toxins and/or water soluble toxins such as one or more of ammonia, urea, aromatic amino acids, manganese, and a benzodiazepine-like substance. The one or more molecules may also or instead include uremic toxins, metabolic waste, and excess water (e.g., extracted from the blood of the first animal when the first animal is a kidney patient). The one or more molecules may also or instead include beneficial molecules (e.g., albumin) extracted from the vascular system of the healthy animal 104 for transfer to the liver patient 102.

The second fluid connectors 132 may be the same or similar to the first fluid connectors 122. Similarly, the second fluid connectors 132, or generally the second extracorporeal circuit 130, may also or instead include devices or components used to gain access to the blood of the healthy animal 104, including without limitation, one or more of an IV catheter, a synthetic graft, and the like. In some implementations, a preliminary procedure may be performed on the liver patient 102 and/or healthy animal 104 to make vascular access more convenient. Such procedures may include, e.g., creating a venous-venous connection, an arterio-arterio connection, an arterio-venous connection including an arterio-venous fistula or graft, inserting an indwelling needle or cannula, a Venflon device or similar, a catheter, a Port-A-Cath device or similar, a peripherally inserted central catheter (PICC), and the like into one or more blood vessels.

In some implementations, the first and/or second fluid connectors 122, 132 may be pre-primed with an anticoagulant such as heparin. This may advantageously reduce the deployment time of the system 100.

As discussed above, the system 100 may include one or more pumps, e.g., a first pump 140 in fluid communication with the first extracorporeal circuit 120 and a second pump 150 in fluid communication with the second extracorporeal circuit 130. In other aspects, the system 100 may include a single pump that is connected to each of the first extracorporeal circuit 120 and the second extracorporeal circuit 130. For example, the system 100 may include a first pump 140 in fluid communication with at least one of the first extracorporeal circuit 120 and the second extracorporeal circuit 130. Whether using a single pump (e.g., the first pump 140), or a plurality of pumps (e.g., the first pump 140 and the second pump 150), the pump(s) may be operable to provide independent, but coordinated, control over the fluid flow in each of the first extracorporeal circuit 120 and the second extracorporeal circuit 130. In some embodiments, the first pump 140 and/or second pump 150 may be positioned on the arterial side or the venous side of the respective extracorporeal circuit. In some embodiments, when a plurality of pumps are utilized there may be a pump on the venous side and the arterial side of the first extracorporeal circuit 120 and/or the second extracorporeal circuit 130.

One or more of the pumps, e.g., the first pump 140 and the second pump 150, may be connected to one or more drivers 160 for driving the pumps. For example, each pump may be operably (e.g., mechanically) coupled to the same driver 160. In this manner, the first pump 140 and the second pump 150 may be mechanically coupled to the driver 160 as shown in the figure. Alternatively, different pumps in the system 100 may be connected to different drivers 160, but this can complicate the system 100 for establishing a predetermined pressure gradient between the first extracorporeal circuit 120 and the second extracorporeal circuit 130 as discussed herein. Thus, it may be preferable that each pump is mechanically coupled to the same driver 160 in the system 100.

So that ultrafiltration (or the like) can be performed, one or more of the first pump 140, the second pump 150, and the driver 160 may be configured to establish a predetermined pressure gradient between the first extracorporeal circuit 120 and the second extracorporeal circuit 130. By way of example, the predetermined pressure gradient may be selected to implement or encourage a transfer of molecules across the device 110 from the first extracorporeal circuit 120 to the second extracorporeal circuit 130. The predetermined pressure gradient may also or instead be selected to implement or encourage a transfer of molecules across the device 110 from the second extracorporeal circuit 130 to the first extracorporeal circuit 120. The predetermined pressure gradient may also or instead be selected to implement or encourage a transfer of molecules across the device 110 from both (i) the first extracorporeal circuit 120 to the second extracorporeal circuit 130 and (ii) the second extracorporeal circuit 130 to the first extracorporeal circuit 120. Stated otherwise, the predetermined pressure gradient may be selected to implement a predetermined molecule transfer between the first extracorporeal circuit 120 and the second extracorporeal circuit 130. The pressure gradient may be controllable via the controller 192.

Establishing a pressure gradient, or otherwise promoting the passage of molecules across the semipermeable membrane 116, may be particularly useful when larger molecules are intended for exchange across the semipermeable membrane 116 as described herein. This is because relatively large molecules such as albumin may not diffuse easily. Thus, for an efficient exchange, a relatively strong convective transport may be implemented, which may be at least in part promoted through the establishment of a pressure gradient.

The predetermined pressure gradient may be provided at least in part by a predetermined gear ratio difference between the first pump 140 and the second pump 150. Also, or instead, a gear ratio difference between the first pump 140 and the second pump 150 may be controllable in the system 100. For example, one or more of the first pump 140 and the second pump 150 may include a plurality of gears 142, where different combinations or sets of gears 142 can be selectively used or configured for pumping fluid in the extracorporeal circuits to achieve a predetermined gear ratio and thereby establish a predetermined pressure gradient between the extracorporeal circuits.

To this end, the system 100 may further include one or more selector switches 180. In certain aspects, a selector switch 180 has at least a first setting and a second setting, where the first setting establishes a zero-pressure gradient between the first extracorporeal circuit 120 and the second extracorporeal circuit 130, and where the second setting establishes a nonzero pressure gradient between the first extracorporeal circuit 120 and the second extracorporeal circuit 130. Other settings for different nonzero pressure gradients are also possible using a selector switch 180.

By way of example, the selector switch 180 may be operable to switch between different sets of gears 142 in one or more of the pumps. This is shown by way of representation in the figure, where the first pump 140 includes a first set of gears 144 and a second set of gears 146. The selector switch 180 may be operable to toggle between the first set of gears 144 and a second set of gears 146. In this manner, the selector switch 180 may include a mechanical toggle, a wheel, a slider, a valve, or another similar mechanical input device that switches between sets of gears 142 (or otherwise redirects or adjusts flow) to control a pressure gradient between the first extracorporeal circuit 120 and the second extracorporeal circuit 130 in the system 100. The selector switch 180, or other components in the system 100, may alternatively be electronically operated or controlled, e.g., via the controller 192.

In implementations, the range of available pressure gradients may fall between those affording a standard clinical range of ultrafiltration rates. For example, pressure gradients resulting in an ultrafiltration rate from 0 L/hour to 1 L/hour may be implemented.

The present teachings may also or instead include techniques for alternating the pressure gradients between the kidney patient 102 and the healthy animal 104, e.g., to enhance the flux in one direction and to control the other direction for balancing. This may be achieved using a selector switch 180 or the like as described herein. Similarly, backfiltration within the device 110 may be controllable (e.g., for enhancing backfiltration when desired). Further embodiments are described below (e.g., with reference to FIGS. 8-11) for controlling the flow through the device 110 for desired molecule exchange and diffusion.

Turning back to FIG. 1, the pumps in the system 100 may include any as known in the art of dialysis (e.g., hemodialysis or liver dialysis). For example, one or more of the pumps may include, without limitation, a peristaltic pump (e.g., a roller pump), a syringe pump, a centrifugal pump, and so on. More generally, any pump capable of pumping blood may be used in the system 100. In an aspect, each of the first pump 140 and the second pump 150 include a peristaltic pump; in this manner, it will be understood that the gears 142 described herein and shown in the figure may include rollers or the like instead of "gears" in the traditional sense (e.g., the gears 142 may lack teeth/cogs).

One or more drivers 160 may be used to drive the pumps in the system 100. For example, the driver 160 may be mechanically coupled to the first pump 140, where the driver 160 is configured to drive the first pump 140 using energy from the energy source 170. The driver 160 may similarly be mechanically coupled to the second pump 150, where the driver 160 is configured to drive the second pump 150 using energy from the energy source 170. Thus, the energy source 170 may supply energy to one or more drivers 160 in the system 100.

In implementations, the driver 160 may include a mechanical crank 162, where the energy source 170 is an animal. For example, the mechanical crank 162 may include a hand or foot crank, where the animal acting as the energy source 170 is a human that uses the hand or foot crank to create energy for activating the driver 160 to drive the pump(s). In implementations, the driver 160 may include a motor and a photovoltaic cell, where the energy source is light, e.g., sunlight. In some implementations, the driver 160 includes a motor, where the energy source is a battery or the like. The driver 160, energy source 170, or both, may also or instead be integral with one or more of the pumps or another component of the system 100.

In this manner, as described herein, the system 100 may be operable without the use of grid power, such that the system 100 could be utilized for liver dialysis when disposed in an area lacking relatively easy access to electricity. Also, because the blood of the healthy animal 104 may be used in the system 100 in lieu of dialysate or the like, the system 100 could be utilized for dialysis when disposed in an area lacking relatively easy access to fresh water.

The system 100 may further include one or more other dialysis components 101. The other dialysis components 101 may be disposed on one or more of the first extracorporeal circuit 120 and the second extracorporeal circuit 130, or otherwise disposed in the system 100. The other dialysis components 101 may include, without limitation, one or more of a sensor (in addition to, or instead of, other sensors 190 described herein), a pressure monitor (e.g., an arterial pressure monitor, a venous pressure monitor, and the like), an air trap, an air detector, a connector, a valve, a heparin pump, a saline drip (or other drip, or pharmaceutical solution), a reservoir, a heater, a controller (in addition to, or instead of, other controllers 192 described herein), a resistive element, a reducer, and the like. For example, in an aspect, the pressure differential may be established by adding resistance (through the use of a dialysis component 101 including a resistive element) to the first extracorporeal circuit 120 (e.g., on a blood outlet on the first side 112 of the device 110). This may be accomplished, e.g., by partially closing a valve on the first extracorporeal circuit 120. Thus, the other dialysis component 101 may include a resistive element such as a valve. Stated otherwise, the system 100 may include a resistive element in fluid communication with one or more of the first extracorporeal circuit 120 and the second extracorporeal circuit 130, where the resistive element is configured to establish a predetermined pressure gradient between the first and second extracorporeal circuits.

The system 100 may further include a controller 192. The controller 192 may include, or otherwise be in communication with, a processor 191, a memory 193, a control panel or user interface, and control wiring for controlling one or more of the components of the system 100. Thus, the controller 192 may be operable to control one or more of the components of the system 100.

The controller 192 may be configured to start, stop, and adjust a component of the system 100 such as the pumps, drivers 160, and the energy source 170. The controller 192 may also or instead be configured to lock a function of, or access to, a component of the system 100, or the system 100 generally. Such control from the controller 192 may be based on signals received from one or more of the sensors 190, or instructions received from a user or otherwise. In general, the controller 192 may be electrically coupled in a communicating relationship, e.g., an electronic communication, with any of the components of the system 100. In general, the controller 192 may be operable to control the components of the system 100, and may include any combination of software and/or processing circuitry suitable for controlling the various components of the system 100 described herein including without limitation one or more processors 191, microprocessors, microcontrollers, application-specific integrated circuits, programmable gate arrays, and any other digital and/or analog components, as well as combinations of the foregoing, along with inputs and outputs for transceiving control signals, drive signals, power signals, sensor signals, and the like. In certain implementations, the controller 192 may include the processor 191 or other processing circuitry with sufficient computational power to provide related functions such as executing an operating system, providing a graphical user interface (e.g., to a display coupled to a control panel or another component of the system 100), set and provide rules and instructions for operation of a component of the system 100, convert sensed information into instructions, notifications, and the like, and operate a web server or otherwise host remote operators and/or activity through one or more communications interfaces. In certain implementations, the controller 192 may include a printed circuit board, an Arduino controller or similar, a Raspberry Pi controller or the like, a prototyping board, or other computer related components.

The controller 192 may be a local controller disposed on a component of the system 100, or a remote controller 192 otherwise in communication with the system 100 and its components. For example, one or more of the controller 192 and a user interface in communication with the controller 192 may be disposed on an external resource 196 (e.g., a computing device) in communication with the system 100 over a data network 195.

The processor 191 of the controller 192 may include an onboard processor for a component of the system 100. The processor 191 may also or instead be disposed on a separate computing device or an external resource 196 that is connected to the system 100 or one or more of its components through a data network 195, e.g., using a communications interface, which may include a Wi-Fi transmitter and receiver. The processor 191 may perform calculations, e.g., for adjusting a component of the system 100.

The processor 191 may be any as described herein or otherwise known in the art. The processor 191 may be included on the controller 192, or it may be separate from the controller 192, e.g., it may be included on a computing device or an external resource 196 in communication with the controller 192 or another component of the system 100. In an implementation, the processor 191 is included on, or is in communication with, a server that hosts an application for operating and controlling the system 100.

The memory 193 may be any as described herein or otherwise known in the art. The memory 193 may contain computer code and may store data such as sequences of operation, sequences for notifications and alerts, historical data of the system 100, security data, health data, and so on. The memory 193 may contain computer executable code stored thereon that provides instructions for the processor 191 for implementation, e.g., by the controller 192 or a computing device of the system 100. The memory 193 may include a non-transitory computer readable medium.

The system 100 may further include one or more external resources 196. For example, an external resource 196 may include a computing device (which can be a local or remote computing device in communication with one or more of the components of the system 100 including without limitation the controller 192). The computing device may include a user interface (or the user interface may be included on a control panel or elsewhere in the system 100), e.g., in communication with the controller 192. The user interface may be used, e.g., to lock and unlock the system 100, monitor the system 100, set parameters for operation, or otherwise.

Such a computing device may include any devices within the system 100 operated by operators or otherwise to manage, monitor, communicate with, or otherwise interact with other participants in the system 100. This may include desktop computers, laptop computers, network computers, tablets, smartphones, smart watches or other wearables, PDAs, or any other device (e.g., IoT device) that can participate in the system 100 as contemplated herein. In an implementation, a computing device (and a user interface thereof) is integral with another participant in the system 100.

An external resource 196, such as a computing device, may include or generally provide a user interface, which may include a graphical user interface, a text or command line interface, a voice-controlled interface, and/or a gesture-based interface. In general, the user interface may create a suitable display (e.g., on a computing device) for operator interaction. In implementations, the user interface may control operation of one or more of the components of the system 100, as well as provide access to and communication with the controller 192, processor 191, and other resources.

Such a user interface may be maintained by a locally executing application on a computing device (e.g., tablet) that receives data from one or more of the components of the system 100 or other resources. In other embodiments, such a user interface may be remotely served and presented on a computing device, such as where the controller 192 includes a web server that provides information through one or more web pages or the like that can be displayed within a web browser or similar client executing on a computing device. In implementations, such a user interface may also or instead be provided by and/or disposed on another participant in the system 100.

The data network 195 may be any network(s) or inter-network(s) suitable for communicating data and control information among participants in the system 100. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMAX-Advanced (IEEE 802.16m) and/or other technologies, as well as any of a variety of corporate area or local area networks and other switches, routers, hubs, gateways, and the like that might be used to carry data among participants in the system 100. The data network 195 may include wired or wireless networks, or any combination thereof. One skilled in the art will also recognize that the participants shown the system 100 need not be connected by a data network 195, and thus can be configured to work in conjunction with other participants independent of the data network 195.

Communication over the data network 195, or other communication between components of the devices or systems described herein, may be provided via one or more communications interfaces. The communications interface may include, e.g., a Wi-Fi receiver and transmitter to allow the logic calculations to be performed on a separate computing device. This may include connections to smartphone applications and the like. More generally, the communications interface may be suited such that any of the components of the system 100 can communicate with one another. Thus, such a communications interface may be present on one or more of the components of the system 100. The communications interface may include, or be connected in a communicating relationship with, a network interface or the like. The communications interface may include any combination of hardware and software suitable for coupling the components of the system 100 to a remote device (e.g., an external resource 196 such as a remote computer or the like) in a communicating relationship through a data network 195. By way of example and not limitation, this may include electronics for a wired or wireless Ethernet connection operating according to the IEEE 802.11 standard (or any variation thereof), or any other short or long range wireless networking components or the like. This may include hardware for short range data communications such as Bluetooth or an infrared transceiver, which may be used to couple into a local area network or the like that is in turn coupled to a data network 195 such as the internet. This may also or instead include hardware/software for a WiMAX connection or a cellular network connection (using, e.g., CDMA, GSM, LTE, or any other suitable protocol or combination of protocols). Additionally, the controller 192 may be configured to control participation by the components of the system 100 in any network to which such a communications interface is connected, such as by autonomously connecting to the data network 195 to retrieve status updates and the like.

The system 100 may include other external resources 196 in the form of other hardware. In certain implementations, this other hardware may include a camera, other sensor or monitor, or the like. The camera may allow a user to view the system 100 in real-time, or to view recorded information, where such information may be stored on the memory 193. This can enable a user to gauge the efficacy or security of the system 100. The other hardware may also or instead include input devices such as a keyboard, a touchpad, a computer mouse, a switch, a dial, a button, and the like, as well as output devices such as a display, a speaker or other audio transducer, light emitting diodes or other lighting or display components, and the like. Other hardware of system 100 may also or instead include a variety of cable connections and/or hardware adapters for connecting to, e.g., external computers, external hardware, external instrumentation or data acquisition systems, and the like.

In general, the system 100 may include communication of one or more components therein over a data network 195, wired or wireless. This may include a self-healing network, such as a mesh network based on low-power Bluetooth or the like. The system 100 may include automatic alerts sent to users, e.g., when one or more of the sensors 190 are triggered. The system 100 may integrate with a graphical user interface on a computing device such as a computer, control station, or mobile phone. The system 100 may perform analytics—e.g., long-term analytics. The system 100 may recognize patterns, e.g., using baseline pattern recognition. The system 100 may be able to locate errors, unsafe conditions, or security conditions. The system 100 may be able to detect other anomalies. The system 100 may be capable of modeling and training sensor sensitivity for local activity to reduce false positives. The system 100 may include one or more alarms, which can be triggered by the one or more sensors 190. The system 100 may be capable of being placed in one or more modes, such as a locked mode.

As discussed herein, the system 100 may further include one or more sensors 190. A sensor 190 may be in communication with the controller 192 or another component of the system 100, e.g., where the controller 192 is configured to control operation of the system 100 at least in part based upon a signal from a sensor 190. For example, the controller 192 may be configured to start, pause, stop, adjust, unlock, or lock the system 100 or a portion or parameter thereof based upon a signal from a sensor 190.

By way of example, a sensor 190 may include a physiological sensor coupled to one or more of the first animal (e.g., the liver patient 102) and the second animal (e.g., the healthy animal 104). Such a physiological sensor may include an oncotic pressure monitor, e.g., where the oncotic pressure monitor is structurally configured to detect and/or monitor albumin transfer. Such a physiological sensor may also or instead include a blood volume monitor, e.g., where the blood volume monitor is structurally configured to measure protein concentration. Such a blood volume monitor (or another sensor 190) may use ultrasound for monitoring/sensing blood volume. A physiological sensor of the system 100 may also or instead be structurally configured to detect fluid loss in one or more of the first animal and the second animal. A physiological sensor of the system 100 may also or instead be structurally configured to measure bilirubin. A physiological sensor of the system 100 may also or instead be an optical sensor—e.g., for the optical measurement of bilirubin that can allow an operator to assess the instantaneous clearance of bilirubin. An optical sensor may also or instead be used to track the removal of substances that are cleared by the liver (e.g., indocyanine green). A physiological sensor of the system 100 may also or instead be structurally configured to detect and/or monitor a red blood cell count (e.g., hemolysis monitoring). A physiological sensor of the system 100 may also or instead be structurally configured to track the transfer of one or more molecules through the semipermeable membrane 116. Other physiological sensors are also or instead possible, such as a heart rate sensor, a breathing sensor, a blood pressure sensor, an oxygen sensor, and so on.

Continuing with the example of a sensor 190 being a physiological sensor, the controller 192 may be in communication with the physiological sensor, where the controller 192 is configured to control operation of the system 100 at least in part based upon a signal from the physiological sensor. For example, the controller 192 may be configured to pause or stop operation of the system 100 upon receipt of a predetermined signal from the physiological sensor, such as a signal that indicates distress or an otherwise undesirable, unhealthy, or unsafe condition of one or more of the first animal and the second animal or another component of the system 100.

Other types of sensors 190 instead of, or in addition to physiological sensors, are also or instead possible for inclusion in the system 100. For example, the sensors 190 may include one or more of a flow sensor, a pressure sensor, a proximity sensor (and/or a sensor 190 to detect the presence or absence of an object), a light sensor, a chemical sensor, a current or voltage sensor, an environmental sensor, a position sensor, a force sensor, a thermal sensor, a leak detector, an air detector (or other fluid detector), and so on.

By way of example, a sensor 190 may be in communication with the controller 192 for detecting and/or monitoring flow in the system 100 for control thereof by the controller 192—e.g., the controller 192 may be used to control an ultrafiltration rate in the system 100 to target a prescribed fluid balance. This may be advantageous for preventing fluid loss in patients with liver failure that have a depleted intravascular volume. As such, in certain implementations, the controller 192 may be in communication with a pump of the system 100 (e.g., the first pump 140 and/or the second pump 150), where the controller 192 is configured to control a flow rate of one or more of the first extracorporeal circuit 120 and the second extracorporeal circuit 130. The flow rate may be adjustable based on a signal received from a sensor 190 (e.g., one or more physiological sensors coupled to one or more of the first animal and the second animal). A preferred flow rate may be selected to provide a predetermined fluid balance for one or more of the first animal and the second animal.

The system 100 may further include a biometric verification system 194, e.g., where the biometric verification system 194 is configured to identify one or more of the first animal (e.g., the liver patient 102) and the second animal (e.g., the healthy animal 104) to determine a permission for use of the system 100. That is, because there is potential for misuse, exploitation, and/or coercion associated with the system 100, especially when deployed in developing or economically challenged areas, a biometric verification system 194 may be implemented to prevent or mitigate these risks. Using such a biometric verification system 194, first animal and the second animal may be required to be planned or prescribed matches, where each of their identities must be verified before use of the system 100. To this end, the biometric verification system 194 may include one or more of a biometric identifier, a fingerprint scanner, a retinal scanner, a voice identifier, and the like. The biometric verification system 194 may include the use of a treatment prescription file or other identification or permissions information, which may be stored in a local or remote database (which may be included as one of the external resources 196 of the system) associated with, or in communication with, a component of the system 100 such as the controller 192. The biometric verification system 194 may be configured such that a verification is required before the system 100 will allow a treatment (e.g., to start a treatment or to continue a treatment). In other words, in certain implementations, a treatment can only be started if biometric identification of the first animal and the second animal is verified, e.g., concurrently verified. In some scenarios, verification may be routinely repeated throughout a treatment. Such a biometric verification system 194 may prevent an unprescribed person from volunteering or being forced to act as a healthy animal 104. It is envisioned that a prescriber would prescribe or match one or more animals for a liver patient 102, and the biometric verification system 194 can be used to verify the match.

The controller 192 may be in communication with the biometric verification system 194 and one or more other components of the system 100. In this manner, the controller 192 may be configured to prevent or stop operation of one or more other components of the system 100 (e.g., a pump or a driver 160) upon receipt of a predetermined signal from the biometric verification system 194—e.g., a predetermined signal that one or more of the first animal and the second animal is not a match or is otherwise unauthorized to use the system 100. For example, and as discussed above, the biometric verification system 194 may be configured to confirm a compatibility between the first animal and the second animal. To this end, and as discussed above, the biometric verification system 194 may be in communication with a database containing information regarding one or more of the first animal and the second animal. Moreover, and as discussed above, the biometric verification system 194 may be structurally configured to concurrently identify the first animal and the second animal. Also or instead, the biometric verification system 194 may be configured to identify one or more of the first animal and the second animal at least once during operation of the system 100.

Example advantages of the system 100 may include that it can be used without a source of fresh water (or traditional dialysate), and that it can be used without grid power or another external energy source. However, it will be understood that the system 100 may also be supplemented with traditional components in the event that either fresh water (or traditional dialysate) or an external energy source is available. For example, in lieu of mechanically operated drives 160, the system 100 may include electrically-operated drives 160 for the pumps (i.e., the pump(s) may be electrically operated in an embodiment).

Figure 2:
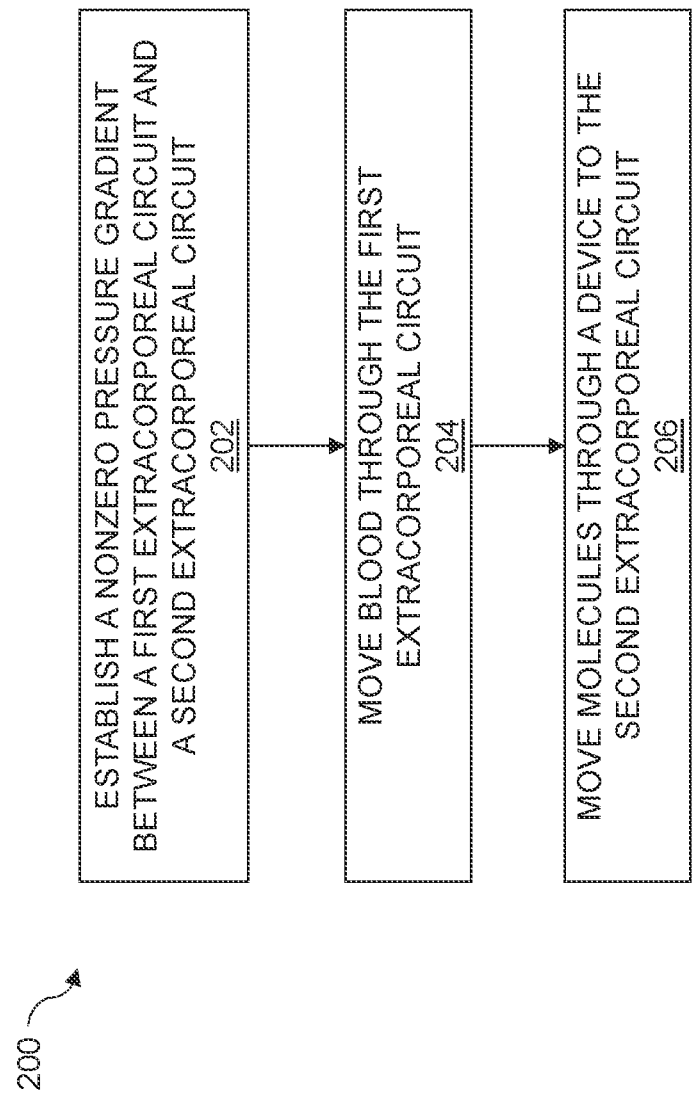
FIG. 2 is a flow chart of a method for performing parabiotic dialysis, in accordance with a representative embodiment.

FIG. 2 is a flow chart of a method for performing parabiotic dialysis, in accordance with a representative embodiment. The method 200 may include the use of a system such as that described in FIG. 1 above, e.g., a liver dialysis system that does not require access to grid power to run the pumps and other components of the system.

As shown in step 202, the method 200 may include establishing a nonzero pressure gradient between a first extracorporeal circuit and a second extracorporeal circuit (e.g., to promote a transfer of molecules from a first extracorporeal circuit to a second extracorporeal circuit). The first extracorporeal circuit may include a first fluid connector that connects a first side of a device to the vascular system of a first animal (e.g., a liver patient), and the second extracorporeal circuit may include a second fluid connector that connects a second side of the device to the vascular system of a second animal (e.g., a healthy animal).

As shown in step 204, the method 200 may include moving blood of the first animal through the first extracorporeal circuit, and as shown in step 206, the method 200 may include moving one or more molecules through the device to the second extracorporeal circuit. The molecules moved from the first extracorporeal circuit to the second extracorporeal circuit may include one or more of albumin, a water-soluble toxin (e.g., one or more of ammonia, urea, aromatic amino acids, manganese, and a benzodiazepine-like substance), and the like. Further, certain molecules may be prevented from moving from the first extracorporeal circuit to the second extracorporeal circuit such as one or more of antibodies, fibrinogen, immunogenic substances, pathogens (e.g., one or more of a virus and bacteria), and the like. The molecules may be moved from the blood of the first animal in the first extracorporeal circuit through the device—more specifically, through a semipermeable membrane of the device—and to the blood of the second animal in the second extracorporeal circuit. To this end, the device may include a semipermeable membrane between its first and second sides. The semipermeable membrane may have an average pore size that allows for the passage of molecules therethrough having a molecular weight of between about 70 kDa and 140 kDa such that the semipermeable membrane is structurally configured for the passage of certain molecules therethrough, and where the semipermeable membrane is structurally configured for the prevention of passage of other, certain molecules therethrough. Also, or instead, the semipermeable membrane may have pores with a pore size structurally configured to allow for the passage of albumin therethrough but to prevent the passage of antibodies therethrough. In this manner, the method 200 may include moving albumin through the device—e.g., from the first extracorporeal circuit to the second extracorporeal circuit—while preventing the movement of antibodies through the device.

It will be understood that, in addition to or instead of the transfer of one or more molecules from the first extracorporeal circuit to the second extracorporeal circuit, one or more molecules may transfer from the second extracorporeal circuit to the first extracorporeal circuit. For example, in certain implementations the first animal is a liver patient and the second animal is a healthy animal, and the method 200 includes movement of healthy and beneficial molecules (e.g., albumin lacking toxins) extracted from the vascular system of the healthy animal and moved through the device for mixing with the blood of the liver patient.

Figure 3:
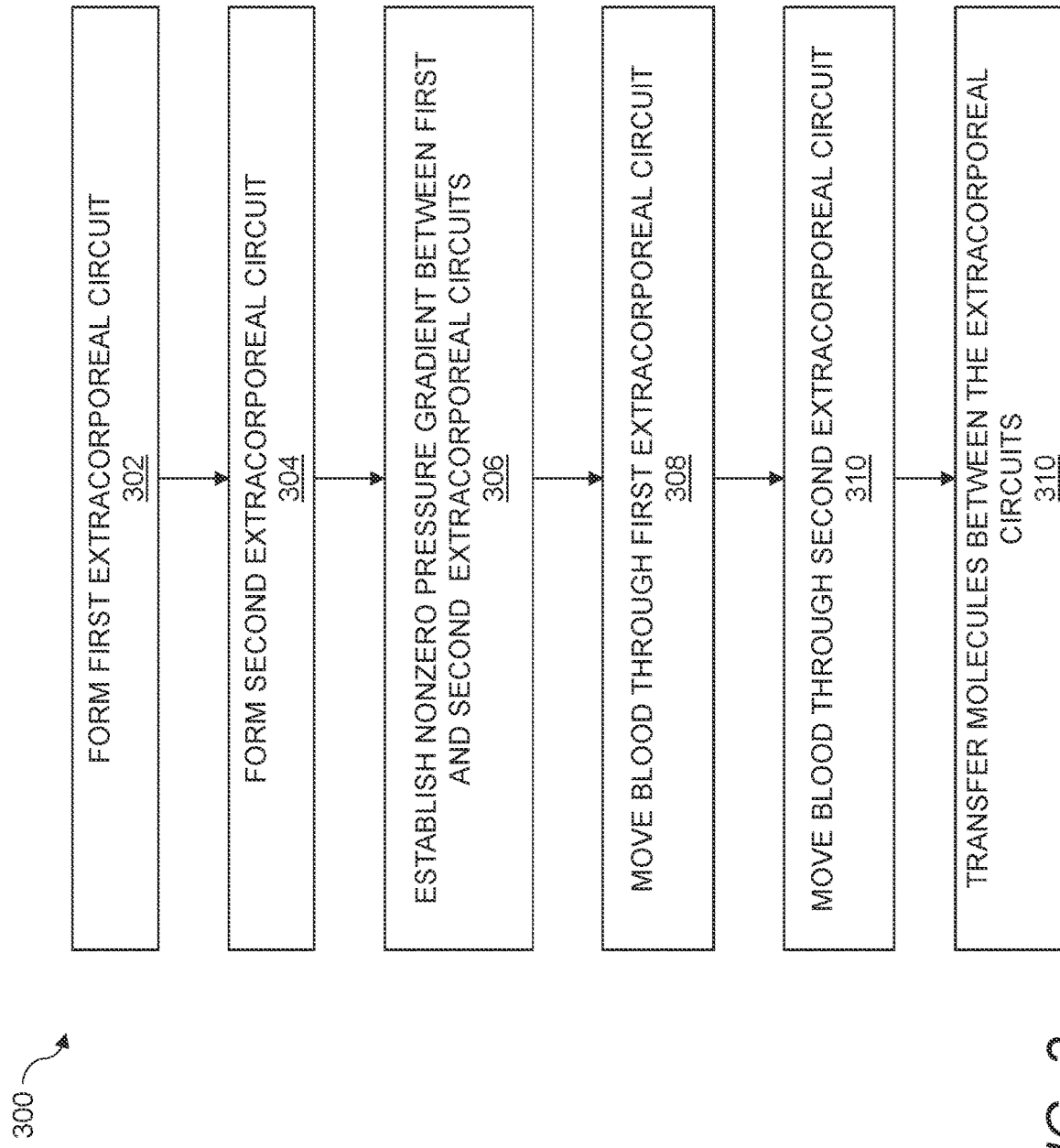
FIG. 3 is a flow chart of a method for parabiotic dialysis, in accordance with a representative embodiment.

FIG. 3 is a flow chart of a method for parabiotic dialysis, in accordance with a representative embodiment. Similar to the method described above with reference to FIG. 2, the method 300 of FIG. 3 may include the use or setup of a system such as that described in FIG. 1 above, e.g., a liver dialysis system that does not require access to grid power to run the pumps and other components of the system.

As shown in step 302, the method 300 may include connecting a first side of a device to the vascular system of a first animal (e.g., a liver patient) to form a first extracorporeal circuit. The device may include a semipermeable membrane between its first side and a second side of the device. The semipermeable membrane may have an average pore size that allows for the passage of molecules having a molecular weight of between about 70 kDa and 140 kDa such that the semipermeable membrane is structurally configured for the passage of one or more molecules therethrough. The semipermeable membrane may also or instead include pores with a pore size structurally configured to allow for the passage of albumin therethrough. The semipermeable membrane may also or instead include pores with a pore size structurally configured to prevent the passage of antibodies therethrough.

As shown in step 304, the method 300 may include connecting a second side of the device to the vascular system of a second animal to form a second extracorporeal circuit.

As shown in step 306, the method 300 may include establishing a nonzero pressure gradient between the first extracorporeal circuit and the second extracorporeal circuit, e.g., to promote the transfer of one or more molecules (e.g., albumin) from the first extracorporeal circuit to the second extracorporeal circuit and/or vice-versa.

As shown in step 308, the method 300 may include moving blood of the first animal through the first extracorporeal circuit.

As shown in step 310, the method 300 may include moving one or more molecules (e.g., albumin) from the blood of the first animal through the semipermeable membrane to the second extracorporeal circuit and/or vice-versa.

Figure 4:
FIG. 4 is a flow chart of a method for safeguarding a parabiotic dialysis system, in accordance with a representative embodiment.

FIG. 4 is a flow chart of a method for safeguarding a parabiotic dialysis system, in accordance with a representative embodiment. Similar to the methods described above with reference to FIGS. 2 and 3, the method 400 of FIG. 4 may include the use or setup of a system such as that described in FIG. 1 above, e.g., a liver dialysis system. More specifically, the method 400 of FIG. 4 may include the use or setup of a system including: a device having a first side and a second side, where the device includes a semipermeable membrane between the first side and the second side that is structurally configured for the passage of one or more molecules (e.g., albumin) therethrough; a first extracorporeal circuit including one or more first fluid connectors for connecting the first side of the device to the vascular system of a first animal; a second extracorporeal circuit including one or more second fluid connectors for connecting the second side of the device to the vascular system of a second animal; a biometric verification system configured to identify one or more of the first animal and the second animal to determine a permission for use; and a controller in communication with the biometric verification system, where the controller is configured to control operation of the system based on one or more signals received from the biometric verification system related to the permission for use. It will be understood that such an exemplary system utilizing the method 400 of FIG. 4 may include one or more of a liver dialysis system (as described above), a hemodialysis system, or any parabiotic system, generally.

As shown in step 402, the method 400 may include connecting a first side of a device to the vascular system of a first animal to form a first extracorporeal circuit. As discussed herein, the device may include a semipermeable membrane structurally configured for the passage of one or more molecules therethrough. The molecules may include one or more of albumin, uremic toxins, metabolic waste, potassium, phosphate, excess water, and combinations thereof and the like.

To that end, the device may include semipermeable membrane, filter, or absorber, such as those found in typical hemodialysis devices. Also, or instead, the device may include a semipermeable membrane having an average pore size that allows for the passage of molecules having a molecular weight of between about 70 kDa and 140 kDa such that the semipermeable membrane is structurally configured for the passage of one or more molecules such as albumin therethrough. In general, it will be understood that any of the membranes described herein may be used in a device for use with the method 400 of FIG. 4.

As shown in step 404, the method 400 may include connecting a second side of the device to the vascular system of a second animal to form a second extracorporeal circuit.

As shown in step 406, the method 400 may include identifying one or more of the first animal and the second animal, e.g., using a biometric verification system as described herein. To identify (and/or to confirm the identity of) one or more of the first animal and the second animal, the method 400 may involve the use of one or more of a biometric identifier, a fingerprint scanner, a retinal scanner, a voice identifier, an access code (e.g., a password or passcode), a QR scanner, a tag reader, a mechanical key, and the like. The step 406 of identifying one or more of the first animal and the second animal may occur before, during, or after use of the aforementioned device or parabiotic system, and the step 406 of identifying one or more of the first animal and the second animal may occur a plurality of times during a treatment. Identifying one or more of the first animal and the second animal may be useful for determining a permission for use for one or more of the first animal and the second animal as explained below.

As shown in step 408, the method 400 may include determining a permission for use for one or more of the first animal and the second animal, e.g., using a biometric verification system as described herein. The permission may be related to the identity of one or more of the first animal and the second animal. For example, a permission for specific animals may be stored on a database (a local database or a database in communication with a biometric verification system), and once the identity of the animal is known or confirmed, the permission status of the animal may be determined by accessing the database. The permission may be based on a security measure (e.g., verifying whether an animal has duly and voluntarily agreed to be part of a parabiotic treatment) and/or a safety or health measure (e.g., verifying whether certain animals are appropriate matches or candidates for a specific parabiotic treatment). The step 408 of determining a permission for use for one or more of the first animal and the second animal may occur before, during, or after use of the aforementioned device or parabiotic system, and the step 408 of determining a permission for use for one or more of the first animal and the second animal may occur a plurality of times during a treatment.

As shown in step 410, the method 400 may include performing an action based on the results of step 406 and/or step 408 (i.e., identifying one or more of the first animal and the second animal, and/or determining a permission for use for one or more of the first animal and the second animal). For example, when it is determined that there is suitable permission for use for each of the first animal and the second animal, the method 400 may include moving blood of the first animal through the first extracorporeal circuit and moving blood of the second animal through the second extracorporeal circuit. The movement of blood through the device may promote or establish the transfer of one or more molecules between the blood of the first animal and the blood of the second animal, i.e., through the semipermeable membrane. This may include moving one or more molecules from the blood of the first animal through the semipermeable membrane to the second extracorporeal circuit, e.g., for performing a parabiotic dialysis treatment of the first animal.

By way of further example, when it is determined that there is not a permission for use for one or more of the first animal and the second animal, the method 400 may include preventing use of, or stopping use of, the parabiotic system including the aforementioned device and extracorporeal circuits. To this end, a parabiotic system implementing the method 400 may include a controller as described herein, where the controller is configured to prevent or stop operation of the system when there is an indication that one or more of the first animal and the second animal lacks the permission or cannot be identified, and where the controller is configured to permit operation of the system when there is an indication that each of the first animal and the second animal has appropriate permissions and/or identifications.

The devices and systems described herein may utilize the teachings of co-pending International Patent Application No. PCT/CN2018/108602 filed on Sep. 29, 2018, and published on Apr. 2, 2020 as WO2020/062135, the entirety of which is hereby incorporated by reference in its entirety.

FIG. 5 illustrates a device for parabiotic dialysis, in accordance with a representative embodiment. It will be understood that the device 500 shown in FIG. 5 may be the same or similar to the device 110 shown and described with reference to FIG. 1, or the device 500 shown in FIG. 5 may be used in lieu of (or in conjunction with) the device 110 shown and described with reference to FIG. 1. Turning back to the device 500 shown in FIG. 5, such a device 500 may be used in a parabiotic dialysis system such as any of those described herein. The device 500 may include a plurality of chambers with at least a portion of a first extracorporeal circuit 520 and a second extracorporeal circuit 530 disposed through the device 500 (e.g., disposed at least partially through one of the chambers of the device 500). The device 500 may also include a semipermeable membrane 516, which may be disposed within one or more of the plurality of chambers of the device 500. The semipermeable membrane 516 may be the same or similar to any of the membranes described herein.

As discussed above, the device 500 may include a plurality of chambers. For example, the device 500 may include a first chamber 501, a second chamber 502, and a third chamber 503. It will be understood that more or less chambers are possible. As shown in the figure, in certain implementations, the first chamber 501 may include at least part of the first extracorporeal circuit 520, the second chamber 502 may include at least part of the second extracorporeal circuit 530, and the third chamber 503 may be disposed at least partially between the first chamber 501 and the second chamber 502. The third chamber 503 may include the semipermeable membrane 516 as shown in the figure. Also, or instead, the third chamber 503 may include one or more of a different membrane, an interface medium, an absorber, or the like. Also, or instead, one or more of the first chamber 501 and the second chamber 502 may include one or more of a membrane (e.g., the semipermeable membrane 516), an interface medium, an absorber, or the like.

FIG. 6 illustrates a cross-sectional view of a device for parabiotic dialysis, in accordance with a representative embodiment. Similar to the figure above, the device 600 provided by way of example in FIG. 6 may include a first chamber 601, a second chamber 602, and a third chamber 603. Moreover, similar to the figure above, the first chamber 601 may include at least part of a first extracorporeal circuit 620, the second chamber 602 may include at least part of a second extracorporeal circuit 630, and the third chamber 602 may be disposed at least partially between the first chamber 601 and the second chamber 602. One or more of the plurality of chambers of the device 600 may include a semipermeable membrane, filter, absorber, other interface media, or a combination thereof. Specifically, as shown in the figure, each of the first chamber 601, the second chamber 602, and the third chamber 603 may include a semipermeable membrane—i.e., as shown in the figure, the first chamber 601 may include a first membrane 604, the second chamber 602 may include a second membrane 605, and the third chamber 603 may include a third membrane 606. One or more of these membranes may be the same, or all of these membranes may be different. For example, the third membrane 606 may include a semipermeable membrane having pores with a pore size structurally configured to allow for the passage of albumin therethrough and/or structurally configured to prevent the passage of antibodies therethrough (e.g., a semipermeable membrane having an average pore size that allows for the passage of molecules having a molecular weight of between about 70 kDa and 140 kDa), and the first membrane 604 and the second membrane 605 may be different semipermeable membranes.

FIG. 7 illustrates a cross-sectional view of a device for parabiotic dialysis, in accordance with a representative embodiment. Similar to the figures above, the device 700 provided by way of example in FIG. 7 may include a first chamber 701, a second chamber 702, and a third chamber 703. Moreover, similar to the figure above, the first chamber 701 may include at least part of a first extracorporeal circuit 720, the second chamber 702 may include at least part of a second extracorporeal circuit 730, and the third chamber 702 may be disposed at least partially between the first chamber 701 and the second chamber 702. More specifically, and as shown in the figure, the third chamber 703 may (at least partially) surround the first chamber 701 and the second chamber 702.

One or more of the plurality of chambers of the device 700 may include a semipermeable membrane, filter, absorber, other interface media, or a combination thereof. For example, one or more of the first chamber 701 and the second chamber 702 may include a semipermeable membrane (e.g., a first membrane 704 and a second membrane 705, which may be the same or different semipermeable membranes). By way of example, one or more of the first membrane 704 and the second membrane 705 may include a semipermeable membrane having pores with a pore size structurally configured to allow for the passage of albumin therethrough and/or structurally configured to prevent the passage of antibodies therethrough (e.g., a semipermeable membrane having an average pore size of between about 70 kDa and 140 kDa). It is also or instead possible that one or more of the first chamber 701 and the second chamber 702 may be devoid of any such membranes.

The third chamber 703 may also or instead include a semipermeable membrane, filter, absorber, another medium, or a combination thereof. In certain implementations—e.g., implementations where one or more of the first membrane 704 and the second membrane 705 include a semipermeable membrane—the third chamber 703 may include an interface media 706. The interface media 706 may be used to accommodate indirect communication of the contents of the first extracorporeal circuit 720 and the second extracorporeal circuit 730. By way of example, the interface media 706 may be a fluid. For example, the fluid of the interface media 706 may include an electrolyte solution such as a saline solution or the like. The fluid of the interface media 706 may have a predetermined flow, e.g., where the fluid of the interface media 706 flows in a circulation loop or the like. To that end, a system including the device 700 may include a pump or the like to create the flow of the fluid of the interface media 706 in one or more chambers of the device, e.g., to promote a mixing or other communication of contents of certain chambers. Also, or instead, a system including the device 700 may include a balancing device, configured to balance a fluid flow within the device 700, its chambers, and/or the extracorporeal circuits.

It will be understood that the membranes included in any of the chambers of the devices of FIGS. 5-7 (or the membranes of other devices discussed herein) may include a membrane formed at least partially by a grouping of membranes (e.g., a grouping of hollow fibers, which itself may include one or more sub-groupings of hollow fibers, arranged in a random or predetermined manner), a flat membrane, a spiral membrane, a cylindrical membrane, or a combination thereof.

As described herein, the present teachings include techniques and systems for parabiotic dialysis that is structurally configured for the passing (e.g., for diffusion) of relatively large molecules (e.g., albumin) from one patient to another patient (e.g., from a liver patient to a healthy animal, and/or vice-versa). However, and as discussed above, these relatively large molecules such as albumin may not diffuse easily, and for an efficient exchange of these molecules across a dialysis device, a relatively strong convective transport may need to be established, which may utilize similar techniques to hemofiltration or hemodiafiltration to enhance molecule passage through a membrane. FIGS. 8A-11 described below are examples of systems utilizing such techniques. It will be understood, however, that FIGS. 8A-11 are provided by way of example and not of limitation, meaning that there are many configurations for various components in the systems described herein that could be used for achieving certain flow and filtration characteristics such as enhancing or mitigating backfiltration, altering pressure gradients to enhance flux in certain directions, balancing the system, and so on.

Figure 8A:
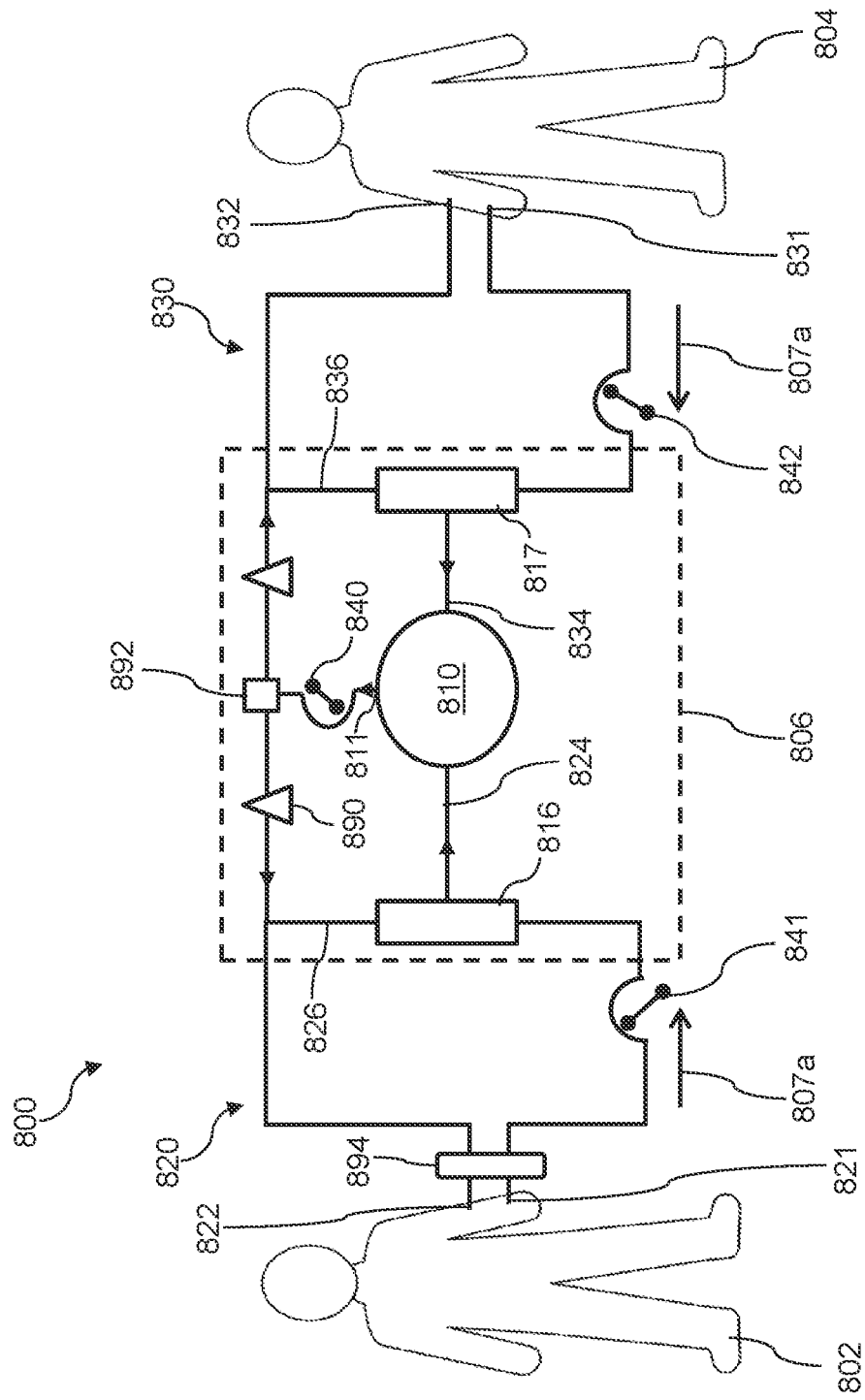
FIG. 8A illustrates a system for parabiotic dialysis, in accordance with a representative embodiment.

FIG. 8A illustrates a system for parabiotic dialysis, in accordance with a representative embodiment. The system 800 may be similar to the other systems described herein, e.g., where the system 800 is used to perform liver dialysis, and/or other forms of dialysis such as hemodialysis. Thus, the system 800 may include a parabiotic liver dialysis system. The system 800 may generally include a first animal 802 (e.g., a liver patient), a second animal 804 (e.g., a healthy animal), a mixing chamber 810, a first extracorporeal circuit 820 featuring a first filter 816, a second extracorporeal circuit 830 featuring a second filter 817, one or more pumps 840, one or more flow sensors 890, a safety filter 892, and a balancer 894. It will be understood that one or more of the components of FIG. 8A (or of any of the components of FIGS. 8A-11, for that matter) may also or instead include any of the features described with reference to FIG. 1 or otherwise described herein, and vice-versa. For example, one or more of the pumps 840 and flow sensors 890 of FIG. 8A may be in communication with a controller similar to that described with reference to FIG. 1.

The first extracorporeal circuit 820 may include a first outlet 821 and a first inlet 822 connecting the first extracorporeal circuit 820 to the vascular system of the first animal 802. In this context, the outlets (e.g., the first outlet 821, or the second outlet 831 described below) may generally include ports or the like where blood flows out from the animals, and the inlets (e.g., the first inlet 822, or the second inlet 832 described below) may generally include ports or the like where blood flows into the animals. The first extracorporeal circuit 820 may further include one or more pumps 840, e.g., a first pump 841 structurally configured to move blood through the first extracorporeal circuit 820 between the first outlet 821 and the first inlet 822.

Similarly, the second extracorporeal circuit 830 may include a second outlet 831 and a second inlet 832 connecting the second extracorporeal circuit 830 to the vascular system of the second animal 804. The second extracorporeal circuit 830 may further include one or more pumps 840, e.g., a second pump 842 structurally configured to move blood through the second extracorporeal circuit 830 between the second outlet 831 and the second inlet 832.

In the system 800, the filters (one or more of the first filter 816 and the second filter 817) may be structurally configured to filter one or more molecules from blood flowing through the respective extracorporeal circuit to which the filter is in communication. For example, a filter may be structurally configured to extract/filter albumin fractions from blood of the first animal 802 for mixing in the mixing chamber 810, e.g., for diffusion into the blood of the second animal 804. To this end, one or more of the filters may include a semipermeable membrane as described herein, e.g., a semipermeable membrane having pores with a pore size that allows for passage of molecules therethrough having a molecular weight of between about 70 kDa and 140 kDa. In an aspect, unfiltered portions of blood may simply flow through (or around) the filter (i.e., without passing through the semipermeable membrane of the filter)—to this end, the filters may include hollow tube filters or the like, where unfiltered blood passes through the core of the filter, while filtered blood passes through the pores of the semipermeable membrane.

It will be understood that the filters may also or instead be integral with the mixing chamber 810. It will also be understood that the first filter 816 and the second filter 817 may be the same type of filter, or they may be different filters.

Components such as pumps 840 and flow sensors 890 in the system 800 (e.g., with the assistance of a controller or the like such as any of the controllers described herein) may be configured to provide for a predetermined exchange of molecules between the circuits and animals. To this end, the system 800 (or any of the systems described herein) may include a filtering circuit 806 containing one or more of the aforementioned components.

The filtering circuit 806 may be in fluid communication with the first extracorporeal circuit 820 and the second extracorporeal circuit 830. Thus, in this context, in the system 100 of FIG. 1, the device 110 of FIG. 1 (or the various devices shown with reference to FIGS. 5-7) may be thought of as a filtering circuit, or a portion of such a filtering circuit. Turning back to FIG. 8A, the filtering circuit 806 may include a first filter 816 including a first semipermeable membrane having first pores, where the first filter 816 is structurally configured to filter blood from the first animal 802 flowing through the first extracorporeal circuit 820. Similarly, the filtering circuit 806 may include a second filter 817 including a second semipermeable membrane having second pores, where the second filter 817 is structurally configured to filter blood from the second animal 804 flowing through the second extracorporeal circuit 830. In an aspect where the system 800 is structurally configured for liver dialysis, at least some pores of one or more of the first pores and the second pores have a pore size structurally configured to allow for passage of albumin therethrough—e.g., each of the first filter 816 and the second filter 817 may be structurally configured to permit albumin to pass through pores of the membrane contained therein for exchange of albumin between the first animal 802 and the second animal 804. As discussed herein, blood that is unfiltered may simply pass through or around the filters, i.e., not passing through the pores of the membrane(s) contained therein.

In an implementation, blood (e.g., filtered blood) may be mixed (e.g., in the mixing chamber 810 in the system of FIG. 8A) using one or more bypasses that fluidly connect the first extracorporeal circuit 820 and the second extracorporeal circuit 830. That is, in the system 800, such bypasses may provide blood from the first extracorporeal circuit 820 and the second extracorporeal circuit 830 for mixing, e.g., in the mixing chamber 810 or directly within an opposing extracorporeal circuit.

More specifically, the system 800 may include a first bypass 824 connecting the first extracorporeal circuit 820 to the second extracorporeal circuit 830, e.g., through the mixing chamber 810. To this end, the first extracorporeal circuit 820 may be configured such that a first blood portion flowing through the first filter 816 without passing through the first pores flows back into the vascular system of the first animal 802 through the first extracorporeal circuit 820—specifically, in the system 800 of FIG. 8A, this first blood portion would flow through segment 826. Further, to this end, the first extracorporeal circuit 820 may be configured such that a second blood portion passing through the first pores of the first filter 816 flows through the first bypass 824 and into the second extracorporeal circuit 830 (e.g., through the mixing chamber 810) for entering the vascular system of the second animal 804—specifically, in the system 800 of FIG. 8A, the second blood portion (e.g., after mixing) would exit the mixing chamber 810 (e.g., assisted by a pump 840) through its outlet 811 for flowing back into one or more of the first extracorporeal circuit 820 and the second extracorporeal circuit 830.

Similarly, the system 800 may include a second bypass 834 connecting the second extracorporeal circuit 830 to the first extracorporeal circuit 820, e.g., through the mixing chamber 810. To this end, the second extracorporeal circuit 830 may be configured such that a third blood portion flowing through the second filter 817 without passing through the second pores flows back into the vascular system of the second animal 804 through the second extracorporeal circuit 830—specifically, in the system 800 of FIG. 8A, this third blood portion would flow through segment 836. Further, to this end, the second extracorporeal circuit 830 may be configured such that a fourth blood portion passing through the second pores of the second filter 817 flows through the second bypass 834 and into the first extracorporeal circuit 820 (e.g., through the mixing chamber 810) for entering the vascular system of the first animal 802—specifically, in the system 800 of FIG. 8A, the fourth blood portion (e.g., after mixing) would exit the mixing chamber 810 (e.g., assisted by a pump 840) through its outlet 811 for flowing back into one or more of the first extracorporeal circuit 820 and the second extracorporeal circuit 830.

As discussed above and as shown in FIG. 8A, the filtering circuit 806 may include a mixing chamber 810. The mixing chamber 810 may be in fluid communication with each of the first filter 816 and the second filter 817, where the mixing chamber 810 is structurally configured to receive filtered blood from the first animal 802 and filtered blood from the second animal 804 for mixing within the mixing chamber 810. An outlet 811 of the mixing chamber 810 may be in fluid communication with one or more of the first extracorporeal circuit 820 and the second extracorporeal circuit 830 for supplying mixed blood to one or more of the first extracorporeal circuit 820 and the second extracorporeal circuit 830. For example, and as shown in the figure, the outlet 811 of the mixing chamber 810 may be in fluid communication with each of the first extracorporeal circuit 820 and the second extracorporeal circuit 830 for supplying mixed blood to each of the first extracorporeal circuit 820 and the second extracorporeal circuit 830. In certain aspects, the mixing chamber 810 includes a plurality of outlets, e.g., one for returning blood to each extracorporeal circuit. The mixing chamber 810 may include a container or housing that can be specifically tailored for blood mixing. In other aspects, the mixing chamber 810 is merely a tube or a series of connected tubes/tubing.

The system 800 may further include a pump 840 disposed between the outlet 811 of the mixing chamber 810 and one or more of the first extracorporeal circuit 820 and the second extracorporeal circuit 830. Also or instead, the system 800 may further include a filter (e.g., a safety filter 892 for preventing blood leaks or the like) disposed between the outlet 811 of the mixing chamber 810 and one or more of the first extracorporeal circuit 820 and the second extracorporeal circuit 830. Such a safety filter 892 may also or instead be disposed in other portions of the system 800.

The system 800 may further include one or more flow control devices 890 between the outlet 811 of the mixing chamber 810 and one or more of the first extracorporeal circuit 820 and the second extracorporeal circuit 830 (e.g., between the outlet 811 of the mixing chamber 810 and each of the first extracorporeal circuit 820 and the second extracorporeal circuit 830). The flow control devices 890 may include a valve, a resistive element, or the like. The flow control devices 890 may also or instead include, or be in communication with, one or more sensors (e.g., pressure sensors, flow sensors, and the like).

The system 800 may further include a balancer 894 for further control of a volume of blood entering and/or exiting one or more of the first animal 802 and the second animal 804, or otherwise for controlling a volume of flow in the system 800. Thus, the system 800 may include a balancer 894 in fluid communication with one or more of the first extracorporeal circuit 820 and the second extracorporeal circuit 830. The balancer 894 may include one or more flow control devices.

Figure 8B:
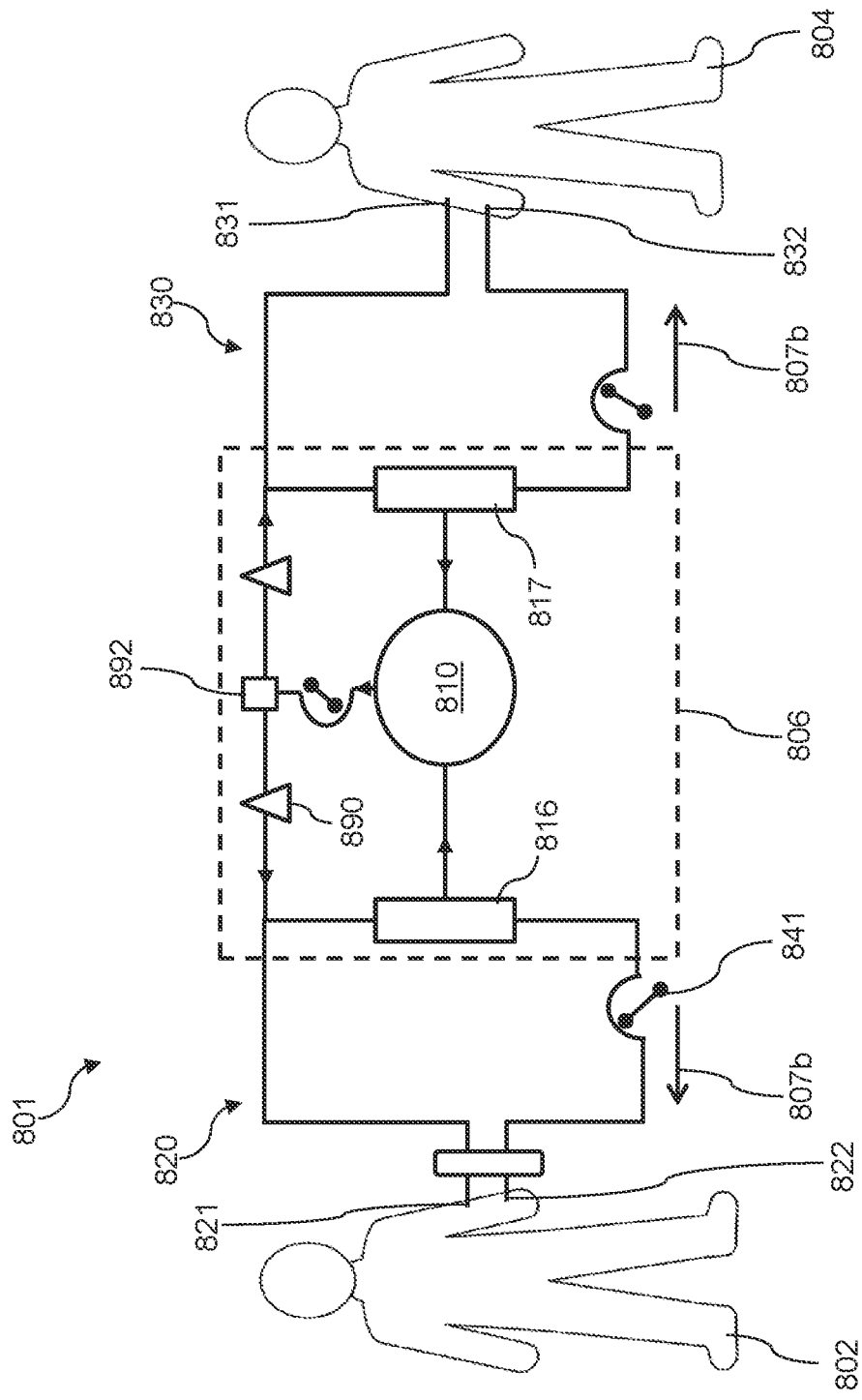
FIG. 8B illustrates a system for parabiotic dialysis, in accordance with a representative embodiment.

FIG. 8B illustrates a system for parabiotic dialysis, in accordance with a representative embodiment. The system 801 of FIG. 8B may be similar to the system 800 of FIG. 8A, and may thus include the same (or similar) components.

However, while FIG. 8A illustrates a post-dilution type of a system 800, FIG. 8B illustrates a pre-dilution type of a system 801. That is, a difference between the system 800 of FIG. 8A and the system 801 of FIG. 8B may be the direction of the flow in the circuits (where the flow is illustrated by the direction of arrows 807a in FIG. 8A and arrows 807b in FIG. 8B). Similarly, the outlets and inlets connected to the first animal 802 and the second animal 804 may be reversed in FIG. 8B compared to FIG. 8A. In general, because of being a pre-dilution type of a system 801, the system 801 of FIG. 8B may require a starting solution to be present in the circuits before commencing use. That is, the system 801 may include a solution that is present within the first extracorporeal circuit 820 before blood from the first animal 802 traverses through the first extracorporeal circuit 820, and a similar solution may also or instead be present within the second extracorporeal circuit 830.

Also, in this manner, in the system 800 of FIG. 8A, the first pump 841 may be disposed between the first outlet 821 and the first filter 816, while in the system 801 of FIG. 8B, the first pump 841 may be disposed between the first filter 816 and the first inlet 822.

Figure 9:
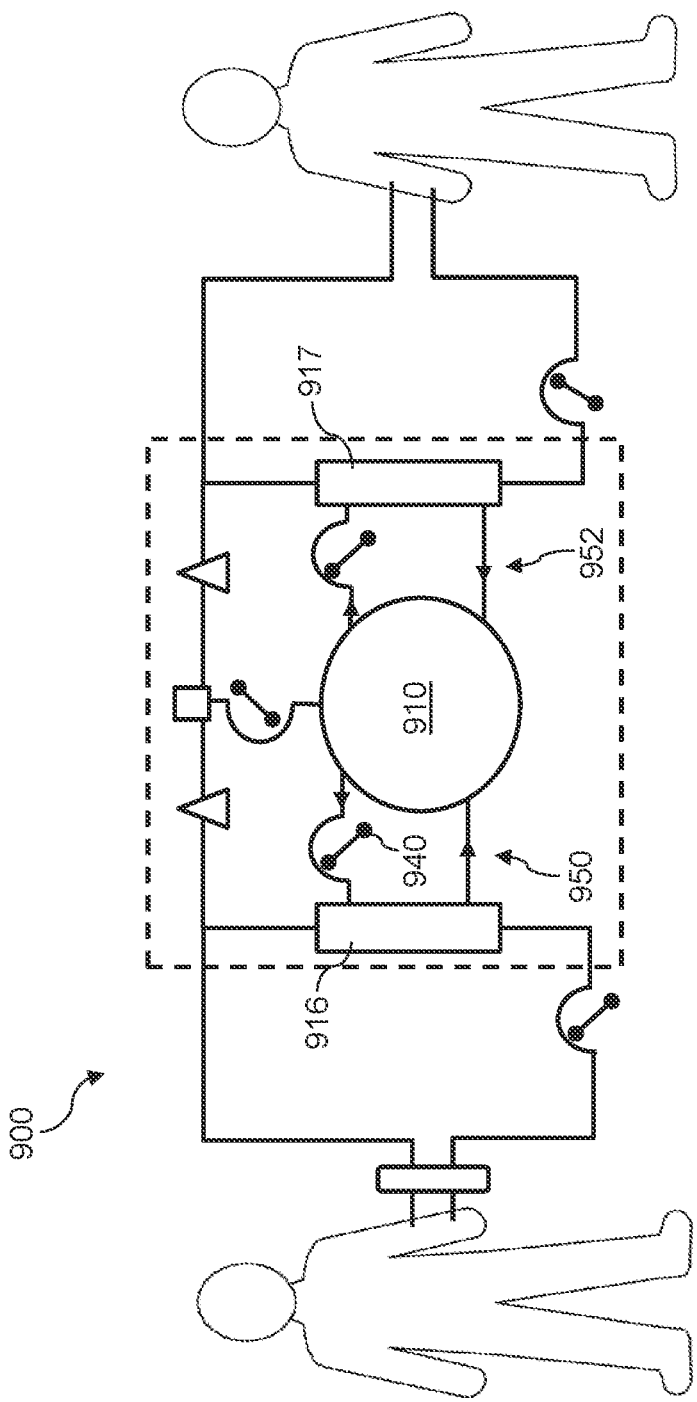
FIG. 9 illustrates a system for parabiotic dialysis, in accordance with a representative embodiment.

FIG. 9 illustrates a system for parabiotic dialysis, in accordance with a representative embodiment. The system 900 of FIG. 9 may be similar to that described above with reference to FIGS. 8A and 8B, but with more robust flow control through the use of additional pumps 940, e.g., for hemodiafiltration. By way of example, in FIG. 9, pumps 940 are included between the mixing chamber 910 and the filters (the first filter 916 and the second filter 917, respectively) to promote a predetermined flow. The system 900 may also advantageously provide a decrease in potential backfiltration.

More specifically, the system 900 of FIG. 9 may include a third extracorporeal circuit 950 including the first filter 916 and the mixing chamber 910. The third extracorporeal circuit 950 may be structurally configured such that filtered blood travels from the first filter 916 into the mixing chamber 910 (e.g., through a bypass as described above with reference to FIG. 8A) and mixed blood is returned to the first filter 916 from the mixing chamber 910. To help further promote flow through the third extracorporeal circuit 950, and thus through the first filter 916, the third extracorporeal circuit 950 may include a pump 940. This pump 940 may be disposed along a portion of the third extracorporeal circuit 950 through which mixed blood is returned to the first filter 916 from the mixing chamber 910. It is also or instead possible for a pump to be disposed along the bypass (i.e., along the line supplying filtered blood from the first filter 916 into the mixing chamber 910).

Similarly, the system 900 of FIG. 9 may include a fourth extracorporeal circuit 952 including the second filter 917 and the mixing chamber 910. The fourth extracorporeal circuit 952 may be structurally configured such that filtered blood travels from the second filter 917 into the mixing chamber 910 (e.g., through a bypass as described above with reference to FIG. 8A) and mixed blood is returned to the second filter 917 from the mixing chamber 910. To help further promote flow through the fourth extracorporeal circuit 952, and thus through the second filter 917, the fourth extracorporeal circuit 952 may include a pump 940. This pump 940 may be disposed along a portion of the fourth extracorporeal circuit 952 through which mixed blood is returned to the second filter 917 from the mixing chamber 910. It is also or instead possible for a pump to be disposed along the bypass (i.e., along the line supplying filtered blood from the second filter 917 into the mixing chamber 910).

Figure 10:
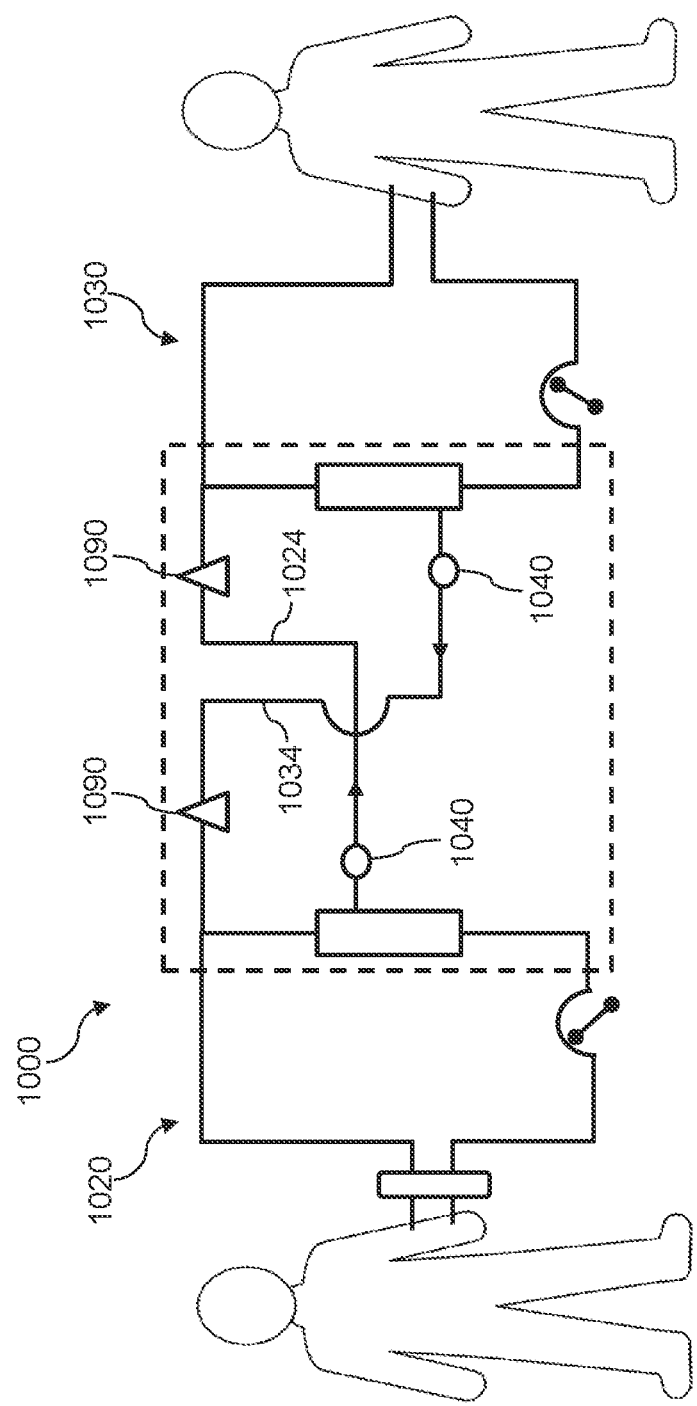
FIG. 10 illustrates a system for parabiotic dialysis, in accordance with a representative embodiment.

FIG. 10 illustrates a system for parabiotic dialysis, in accordance with a representative embodiment. The system 1000 of FIG. 10 may be similar to those described above with reference to FIGS. 8A-9, and may thus include many of the same or similar components, but in the system 1000 of FIG. 10, filtered molecules from the blood are not mixed and (at least partially) returned to the same animal, but instead the molecules are directly infused into the other animal through a bypass. In this manner, as shown in the figure, the first bypass 1024 may be connected directly to the second extracorporeal circuit 1030, and the second bypass 1034 may be connected directly to the first extracorporeal circuit 1030. Also, as shown in the figure, one or more of the first bypass 1024 and the second bypass 1034 may include a pump 1040 (e.g., each of the first bypass 1024 and the second bypass 1034 may include a pump 1040). Also, or instead, one or more of the first bypass 1024 and the second bypass 1034 may include a flow control device 1090 (e.g., each of the first bypass 1024 and the second bypass 1034 may include a flow control device 1090).

Figure 11:
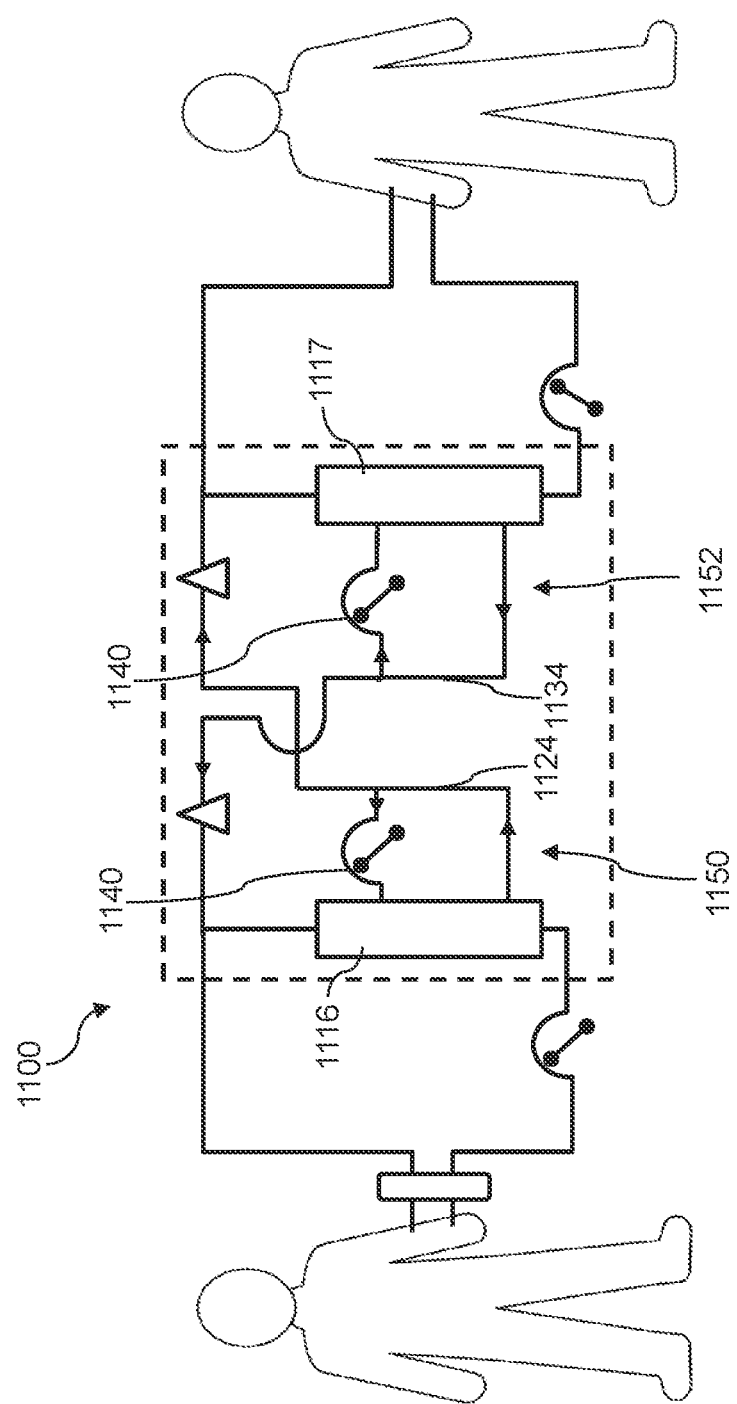
FIG. 11 illustrates a system for parabiotic dialysis, in accordance with a representative embodiment.

FIG. 11 illustrates a system for parabiotic dialysis, in accordance with a representative embodiment. The system 1100 of FIG. 11 may be similar to those described above with reference to FIGS. 8A-10, and may thus include many of the same or similar components. In particular, the system 1100 of FIG. 11 may be similar to that described above with reference to FIG. 10, but with more robust flow control, e.g., for hemodiafiltration.

More specifically, the system 1100 of FIG. 11 may include a third extracorporeal circuit 1150 including the first filter 1116 and the first bypass 1124. The third extracorporeal circuit 1150 may be structurally configured to promote movement of blood through the first filter 1116. To help further promote flow through the third extracorporeal circuit 1150, and thus through the first filter 1116, the third extracorporeal circuit 1150 may include a pump 1140. This pump 1140 may be disposed along a portion of the third extracorporeal circuit 1150 where blood is returned to the first filter 1116 from the first bypass 1124. It is also or instead possible for a pump to be disposed along the outlet from the first filter 1116 (i.e., the line supplying filtered blood from the first filter 1116 to the first bypass 1124).

Similarly, the system 1100 of FIG. 11 may include a fourth extracorporeal circuit 1152 including the second filter 1117 and the second bypass 1134. The fourth extracorporeal circuit 1152 may be structurally configured to promote movement of blood through the second filter 1117. To help further promote flow through the fourth extracorporeal circuit 1152, and thus through the second filter 1117, the fourth extracorporeal circuit 1152 may include a pump 1140. This pump 1140 may be disposed along a portion of the fourth extracorporeal circuit 1152 where blood is returned to the second filter 1117 from the second bypass 1134. It is also or instead possible for a pump to be disposed along the outlet from the second filter 1117 (i.e., the line supplying filtered blood from the second filter 1117 to the second bypass 1134).

Thus, it will be understood that the systems shown and described above with reference to FIGS. 8A-11 may include parabiotic dialysis systems comprising a first extracorporeal circuit including a first outlet and a first inlet connecting the first extracorporeal circuit to the vascular system of a first animal, and a first pump structurally configured to move blood through the first extracorporeal circuit between the first outlet and the first inlet; a second extracorporeal circuit including a second outlet and a second inlet connecting the second extracorporeal circuit to the vascular system of a second animal, and a second pump structurally configured to move blood through the second extracorporeal circuit between the second outlet and the second inlet; and a filtering circuit in fluid communication with the first extracorporeal circuit and the second extracorporeal circuit. The filtering circuit may include a first filter including a first semipermeable membrane having first pores, the first filter structurally configured to filter blood from the first animal flowing through the first extracorporeal circuit; and a second filter including a second semipermeable membrane having second pores, the second filter structurally configured to filter blood from the second animal flowing through the second extracorporeal circuit. Further, it will be understood that the systems shown and described above with reference to FIGS. 8A-11 may include parabiotic dialysis systems further including a first bypass connecting the first extracorporeal circuit to the second extracorporeal circuit, where the first extracorporeal circuit is configured such that a first blood portion flowing through the first filter without passing through the first pores flows back into the vascular system of the first animal through the first extracorporeal circuit, and where a second blood portion passing through the first pores flows through the first bypass and into the second extracorporeal circuit for entering the vascular system of the second animal; and a second bypass connecting the second extracorporeal circuit to the first extracorporeal circuit, where the second extracorporeal circuit is configured such that a third blood portion flowing through the second filter without passing through the second pores flows back into the vascular system of the second animal through the second extracorporeal circuit, and where a fourth blood portion passing through the second pores flows through the second bypass and into the first extracorporeal circuit for entering the vascular system of the first animal. One or more of the first filter and the second filter may include a hemofilter, a hemodialyzer, and/or a semipermeable membrane as described herein.

It will be understood that the present teachings may be used as a treatment for a variety of patients having a variety of disorders/conditions. For example, potential applications for the present teachings may include treatment of liver failure or reduced liver function (acute or chronic, treatment of liver failure to enable liver regeneration or as a bridge to liver transplantation, treatment of neonatal (infant) jaundice, treatment of hepatic encephalopathy, and others. It will be understood that the present teachings may not be suited for other conditions, however. For example, the present teachings may not be suited for poison-type liver failure with substances such as acetaminophen or amanita phalloides toxins.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A parabiotic liver dialysis system, the system comprising:
    a device having a first side and a second side, the device including a semipermeable membrane between the first side and the second side, the semipermeable membrane having an average pore size allowing for passage of molecules having a molecular weight of between about 70 kilodaltons (kDa) and 140 kDa;
    a first extracorporeal circuit including one or more first fluid connectors for connecting the first side of the device to the vascular system of a first animal;
    a second extracorporeal circuit including one or more second fluid connectors for connecting the second side of the device to the vascular system of a second animal;
    a first pump in fluid communication with at least one of the first and second extracorporeal circuits;
    a driver mechanically coupled to the first pump, the driver configured to drive the first pump using energy from an energy source; and
    a plurality of chambers disposed in the device, the plurality of chambers comprising:
        a first chamber including at least part of the first extracorporeal circuit;
        a second chamber including at least part of the second extracorporeal circuit; and
        a third chamber disposed at least partially between the first chamber and the second chamber, wherein the third chamber contains the semipermeable membrane, and wherein each of the first chamber and the second chamber include different semipermeable membranes.

2. The system of claim 1, wherein the molecules include albumin.

3. The system of claim 1, wherein the molecules include a water-soluble toxin.

4. The system of claim 1, wherein the first animal has a liver disorder.

5. The system of claim 1, wherein the first animal has jaundice.

6. The system of claim 1, further comprising:
    a physiological sensor coupled to one or more of the first animal and the second animal; and
    a controller in communication with the physiological sensor, the controller configured to control operation of the system at least in part based upon a signal from the physiological sensor, and to pause or stop operation of the system upon receipt of a predetermined signal from the physiological sensor.

7. The system of claim 1, further comprising a biometric verification system configured to identify one or more of the first animal and the second animal to determine a permission for use of the system.

8. The system of claim 1, further comprising a controller in communication with the first pump, the controller configured to control a flow rate of one or more of the first extracorporeal circuit and the second extracorporeal circuit.

9. The system of claim 1, further comprising a second pump, wherein the first pump is in fluid communication with the first extracorporeal circuit and the second pump is in fluid communication with the second extracorporeal circuit.

10. The system of claim 9, wherein one or more of the first pump, the second pump, and the driver are configured to establish a predetermined pressure gradient between the first and second extracorporeal circuits.

11. The system of claim 10, wherein the predetermined pressure gradient is selected to implement a predetermined molecule transfer between the first extracorporeal circuit and the second extracorporeal circuit.

12. The system of claim 1, further comprising a selector switch having at least a first setting and a second setting, the first setting establishing a zero-pressure gradient between the first and second extracorporeal circuits, and the second setting establishing a nonzero pressure gradient between the first and second extracorporeal circuits.

13. The system of claim 1, further comprising a resistive element in fluid communication with one or more of the first extracorporeal circuit and the second extracorporeal circuit, the resistive element configured to establish a predetermined pressure gradient between the first and second extracorporeal circuits.

14. A method for parabiotic liver dialysis, the method comprising:
    moving blood of a first animal through a first extracorporeal circuit including a first fluid connector that connects a first side of a device to the vascular system of the first animal, the device including a semipermeable membrane having an average pore size allowing for passage of one or more molecules having a molecular weight of between about 70 kilodaltons (kDa) and 140 kDa, the device further including a plurality of chambers comprising a first chamber including at least part of the first extracorporeal circuit, a second chamber, and a third chamber disposed at least partially between the first chamber and the second chamber, wherein the third chamber contains the semipermeable membrane, and wherein each of the first chamber and the second chamber include different semipermeable membranes; and moving the one or more molecules through the device to a second extracorporeal circuit including a second fluid connector that connects a second side of the device to the vascular system of a second animal, wherein the second chamber of the plurality of chambers includes at least part of the second extracorporeal circuit.

15. A method for parabiotic liver dialysis, the method comprising:

connecting a first side of a device to the vascular system of a first animal to form a first extracorporeal circuit, the device including a semipermeable membrane having an average pore size allowing for passage of molecules having a molecular weight of between about 70 kilodaltons (kDa) and 140 kDa, the device further including a plurality of chambers comprising a first chamber including at least part of the first extracorporeal circuit, a second chamber, and a third chamber disposed at least partially between the first chamber and the second chamber, wherein the third chamber contains the semipermeable membrane, and wherein each of the first chamber and the second chamber include different semipermeable membranes; and connecting a second side of the device to the vascular system of a second animal to form a second extracorporeal circuit, wherein the second chamber of the plurality of chambers includes at least part of the second extracorporeal circuit.

16. The method of claim 15, further comprising:

moving blood of the first animal through the first extracorporeal circuit; and moving the one or more molecules from the blood of the first animal through the semipermeable membrane to the second extracorporeal circuit.

* * * * *